US006607916B2

(12) United States Patent
Freier et al.

(10) Patent No.: US 6,607,916 B2
(45) Date of Patent: Aug. 19, 2003

(54) ANTISENSE INHIBITION OF CASEIN KINASE 2-ALPHA EXPRESSION

(75) Inventors: Susan M. Freier, San Diego, CA (US); Jacqualine Wyatt, Encinitas, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/780,172

(22) Filed: Feb. 8, 2001

(65) Prior Publication Data

US 2002/0147163 A1 Oct. 10, 2002

(51) Int. Cl.$^7$ .................. C07H 21/04; A61K 48/00; C12N 15/00
(52) U.S. Cl. ............... 435/375; 435/377; 536/24.1; 536/24.5; 514/44
(58) Field of Search .................. 435/375, 377; 536/24.5; 514/44

(56) References Cited

U.S. PATENT DOCUMENTS 5,998,148 A * 12/1999 Bennett et al. ................ 435/6

OTHER PUBLICATIONS

Andrea D. Branch, TIBS Feb. 23, 1998, pp. 45–50.*
Sudhir Agrawal, TIBTECH, Oct. 1996, vol. 14, pp. 376–387.*
Peter Lorenz et al., Cellular and Molecular Biology Research, vol. 40, Nos. 5/6, pp. 519–527.*
Kuang–Yu Jen et al., Stem Cells, 2000; 18: pp. 307–319.*
Blanquet, Neutrophin–induced activation of casein kinase 2 in rat hippocampal slices, Neuroscience, 1998, 86: 739–749.
Chen et al., The beta subunit of CKII negatively regulates *Xenopus oocyte* maturation, Proc Natl Acad Sci U S A, 1997, 94:9136–9140.
Dupuy et al., Casein kinase 2–mediated phosphorylation of respiratory syncytial virus phosphoprotein P is essential for the transcription elongation activity of the viral polymerase; phosphorylation by casein kinase 1 occurs mainly at Ser(215) and is without effect, J Virol, 1999, 73:8384–8392.
Faust et al., Antisense oligonucleotides against protein kinase CK2–alpha inhibit growth of squamous cell carcinoma of the head and neck in vitro, Head Neck 2000, 22:341–346.
Formby et al., Phosphorylation stabilizes alternatively spliced CD44 mRNA transcripts in breast cancer cells: inhibition by antisense complementary to casein kinase II mRNA, Mol Cell Biochem, 1998, 187:23–31.
Heller–Harrison et al., Cloning and characterization of a cDNA encoding the beta subunit of human casein kinase II, Biochemistry, 1989, 28:9053–9058.
Jakobi et al., Human phosvitin/casein kinase type II. Molecular cloning and sequencing of full–length cDNA encoding subunit beta, Eur J Biochem, 1989, 183:227–233.

Lenard, Host cell protein kinases in nonsegmented negative–strand virus (mononegavirales) infection [In Process Citation], Pharmacol Ther, 1999, 83:39–48.
Lozeman et al., Isolation and characterization of human cDNA clones encoding the alpha and the alpha ' subunits of casein kinase II, Biochemistry, 1990, 29:8436–8447.
Marshak et al., Regulation of protein kinase CKII during the cell division cycle, Cell Mol Biol Res, 1994, 40:513–517.
Meisner et al., Molecular cloning of the human casein kinase II alpha subunit [published erratum appears in Biochemistry 1989 Aug 22;28 (17):7138], Biochemistry 1989, 28:4072–4076.
O'Brien et al., Casein kinase 2 binds to and phosphorylates BRCA1, Biochem Biophys Res Commun, 1999, 260:658–664.
Pepperkok et al., Cell growth stimulation by EGF: inhibition through antisense–oligodeoxynucleotides demonstrates important role of casein kinase II, Exp Cell Res, 1991, 197:245–253.
Perez et al., Casein kinase 2 activity increases in the pre–replicative phase of liver regeneration, FEBS Lett, 1988, 238:273–276.
Pinna, Casein kinase 2: an 'eminence grise' in cellular regulation?, Biochim Biophys Acta, 1990, 1054:267–284.
Pinna et al., Protein kinase CK2 ("casein kinase–2") and its implication in cell division and proliferation, Prog Cell Cycle Res, 1997, 3:77–97.
Pyerin et al., Early cell growth stimulation is inhibited by casein kinase II antisense oligodeoxynucleotides, Ann N Y Acad Sci, 1992, 600:295–297.
Robitzki et al., Human casein kinase II. The subunit alpha protein activates transcription of the subunit beta gene, J Biol Chem, 1993, 268:5694–5702.
Schubert et al., The human immunodeficiency virus type 1 encoded Vpu protein is phosphorylated by casein kinase–2 (CK–2) at positions Ser52 and Ser56 within a predicted alpha–helix–turn–alpha–helix–motif, J Mol Biol, 1994, 236:16–25.
Shayan et al., Theileria–mediated constitutive expression of the casein kinase II–alpha subunit in bovine lymphoblastoid cells, Parasitol Res, 1997, 83:526–532.
Singh, Insulin receptor serine kinase activation by casein kinase 2 and a membrane tyrosine kinase, Mol Cell Biochem, 1993, 121:167–174.
Tawfic et al., Growth stimulus–mediated differential translocation of casein kinase 2 to the nuclear matrix. Evidence based on androgen action in the prostate, J Biol Chem, 1994, 269:24615–24620.

(List continued on next page.)

*Primary Examiner*—Sean McGarry
(74) *Attorney, Agent, or Firm*—Licata & Tyrrell P.C.

(57) ABSTRACT

Antisense compounds, compositions and methods are provided for modulating the expression of Casein kinase 2-alpha. The compositions comprise antisense compounds, particularly antisense oligonucleotides, targeted to nucleic acids encoding Casein kinase 2-alpha. Methods of using these compounds for modulation of Casein kinase 2-alpha expression and for treatment of diseases associated with expression of Casein kinase 2-alpha are provided.

14 Claims, No Drawings

OTHER PUBLICATIONS

Tuazon et al., Casein kinase I and II—multipotential serine protein kinases: structure, function, and regulation, Adv Second Messenger Phosphoprotein Res, 1991, 23:123–164.

Ulloa et al., Depletion of casein kinase II by antisense oligonucleotide prevents neuritogenesis in neuroblastoma cells, Embo J, 1993, 12:1633–1640.

Ulloa et al., Depletion of catalytic and regulatory subunits of protein kinase CK2 by antisense oligonucleotide treatment of neuroblastoma cells, Cell Mol Neurobiol, 1994, 14:407–414.

Wadd et al., The multifunctional herpes simplex virus IE63 protein interacts with heterogeneous ribonucleoprotein K and with casein kinase 2 [In Process Citation], J Biol Chem, 1999, 274:28991–28998.

Watabe et al., Treatment of U937 cells with bufalin induces the translocation of casein kinase 2 and modulates the activity of topoisomerase II prior to the induction of apoptosis, Cell Growth Differ, 1997, 8:871–879.

Yenice et al., Nuclear casein kinase 2 (CK–2) activity in human normal, benign hyperplastic, and cancerous prostate, Prostate, 1994, 24:11–16.

* cited by examiner

SEQUENCE LISTING

```
<160> NUMBER OF SEQ ID NOS: 96

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                           20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                           20

<210> SEQ ID NO 3
<211> LENGTH: 2960
<212> TYPE: DNA
<213> ORGANISM: Homo sapiens
<220> FEATURE:
<221> NAME/KEY: CDS
<222> LOCATION: (507)...(1682)

<400> SEQUENCE: 3
aggggagagc ggccgccgcc gctgccgctt ccaccacaga gaaggaatgt gggcagcctc    60
tagtggcaaa gaccagtccc tggctgacaa ccagaaagaa atgggaccct cagttgtgca   120
accagaagga acctgaattt ggtcaacaac ctgattgagc ttggaagtga atttcccagt   180
ttccaccaag gaatgcaacc ttgagacacc ttgattttg gcctcgtgag accctaagca   240
aaagacctag ctagccaagc ccacccaact tctgacctac ctctatcaag gcttgtcaag   300
cagtgtgctc atcacatggt aaatcatgca gcgtggaacc tcataaaatc tccaagaaac   360
atcattcacc catactgact agtttcacat ctctttgttt gaagaaaaca ggtctgaaac   420 aagtcttac ccccagctgc ttctgaacac agtgactgcc agatctccaa acatcaagtc    480
cagctttgtc cgccaacctg tctgac atg tcg gga ccc gtg cca agc agg gcc    533
                               Met Ser Gly Pro Val Pro Ser Arg Ala
                                 1               5
aga gtt tac aca gat gtt aat aca cac aga cct cga gaa tac tgg gat    581
Arg Val Tyr Thr Asp Val Asn Thr His Arg Pro Arg Glu Tyr Trp Asp
 10              15                  20                  25
tac gag tca cat gtg gtg gaa tgg gga aat caa gat gac tac cag ctg    629
Tyr Glu Ser His Val Val Glu Trp Gly Asn Gln Asp Asp Tyr Gln Leu
             30                  35                  40
```

-continued

| | |
|---|---|
| gtt cga aaa tta ggc cga ggt aaa tac agt gaa gta ttt gaa gcc atc<br>Val Arg Lys Leu Gly Arg Gly Lys Tyr Ser Glu Val Phe Glu Ala Ile<br>               45                        50                    55 | 677 |
| aac atc aca aat aat gaa aaa gtt gtt gtt aaa att ctc aag cca gta<br>Asn Ile Thr Asn Asn Glu Lys Val Val Val Lys Ile Leu Lys Pro Val<br>         60                        65                    70 | 725 |
| aaa aag aag aaa att aag cgt gaa ata aag att ttg gag aat ttg aga<br>Lys Lys Lys Lys Ile Lys Arg Glu Ile Lys Ile Leu Glu Asn Leu Arg<br>   75                       80                    85 | 773 |
| gga ggt ccc aac atc atc aca ctg gca gac att gta aaa gac cct gtg<br>Gly Gly Pro Asn Ile Ile Thr Leu Ala Asp Ile Val Lys Asp Pro Val<br>90                     95                   100            105 | 821 |
| tca cga acc ccc gcc ttg gtt ttt gaa cac gta aac aac aca gac ttc<br>Ser Arg Thr Pro Ala Leu Val Phe Glu His Val Asn Asn Thr Asp Phe<br>                110                   115                 120 | 869 |
| aag caa ttg tac cag acg tta aca gac tat gat att cga ttt tac atg<br>Lys Gln Leu Tyr Gln Thr Leu Thr Asp Tyr Asp Ile Arg Phe Tyr Met<br>             125                   130                135 | 917 |
| tat gag att ctg aag gcc ctg gat tat tgt cac agc atg gga att atg<br>Tyr Glu Ile Leu Lys Ala Leu Asp Tyr Cys His Ser Met Gly Ile Met<br>         140                   145               150 | 965 |
| cac aga gat gtc aag ccc cat aat gtc atg att gat cat gag cac aga<br>His Arg Asp Val Lys Pro His Asn Val Met Ile Asp His Glu His Arg<br>       155                 160               165 | 1013 |
| aag cta cga cta ata gac tgg ggt ttg gct gag ttt tat cat cct ggc<br>Lys Leu Arg Leu Ile Asp Trp Gly Leu Ala Glu Phe Tyr His Pro Gly<br>170                   175               180           185 | 1061 |
| caa gaa tat aat gtc cga gtt gct tcc cga tac ttc aaa ggt cct gag<br>Gln Glu Tyr Asn Val Arg Val Ala Ser Arg Tyr Phe Lys Gly Pro Glu<br>                190                   195              200 | 1109 |
| cta ctt gta gac tat cag atg tac gat tat agt ttg gat atg tgg agt<br>Leu Leu Val Asp Tyr Gln Met Tyr Asp Tyr Ser Leu Asp Met Trp Ser<br>             205                   210                215 | 1157 |
| ttg ggt tgt atg ctg gca agt atg atc ttt cgg aag gag cca ttt ttc<br>Leu Gly Cys Met Leu Ala Ser Met Ile Phe Arg Lys Glu Pro Phe Phe<br>         220                   225               230 | 1205 |
| cat gga cat gac aat tat gat cag ttg gtg agg ata gcc aag gtt ctg<br>His Gly His Asp Asn Tyr Asp Gln Leu Val Arg Ile Ala Lys Val Leu<br>       235                 240               245 | 1253 |
| ggg aca gaa gat tta tat gac tat att gac aaa tac aac att gaa tta<br>Gly Thr Glu Asp Leu Tyr Asp Tyr Ile Asp Lys Tyr Asn Ile Glu Leu<br>250                   255               260           265 | 1301 |
| gat cca cgt ttc aat gat atc ttg ggc aga cac tct cga aag cga tgg<br>Asp Pro Arg Phe Asn Asp Ile Leu Gly Arg His Ser Arg Lys Arg Trp<br>             270                 275              280 | 1349 |
| gaa cgc ttt gtc cac agt gaa aat cag cac ctt gtc agc cct gag gcc<br>Glu Arg Phe Val His Ser Glu Asn Gln His Leu Val Ser Pro Glu Ala<br>         285                 290               295 | 1397 |
| ttg gat ttc ctg gac aaa ctg ctg cga tat gac cac cag tca cgg ctt<br>Leu Asp Phe Leu Asp Lys Leu Leu Arg Tyr Asp His Gln Ser Arg Leu<br>                300                   305              310 | 1445 |
| act gca aga gag gca atg gag cac ccc tat ttc tac act gtt gtg aag<br>Thr Ala Arg Glu Ala Met Glu His Pro Tyr Phe Tyr Thr Val Val Lys<br>         315                 320               325 | 1493 |
| gac cag gct cga atg ggt tca tct agc atg cca ggg ggc agt acg ccc<br>Asp Gln Ala Arg Met Gly Ser Ser Ser Met Pro Gly Gly Ser Thr Pro<br>330                   335               340           345 | 1541 |
| gtc agc agc gcc aat atg atg tca ggg att tct tca gtg cca acc cct<br>Val Ser Ser Ala Asn Met Met Ser Gly Ile Ser Ser Val Pro Thr Pro<br>             350                 355              360 | 1589 |

-continued

| | | | | | | | | | | | | |
|---|---|---|---|---|---|---|---|---|---|---|---|---|
| tca | ccc | ctt | gga | cct | ctg | gca | ggc | tca | cca | gtg | att | gct | gct | gcc | aac | 1637 |
| Ser | Pro | Leu | Gly | Pro | Leu | Ala | Gly | Ser | Pro | Val | Ile | Ala | Ala | Ala | Asn | |
| | | 365 | | | | | 370 | | | | | 375 | | | | |

| ccc | ctt | ggg | atg | cct | gtt | cca | gct | gcc | gct | ggc | gct | cag | cag | taa | 1682 |
| Pro | Leu | Gly | Met | Pro | Val | Pro | Ala | Ala | Ala | Gly | Ala | Gln | Gln | | |
| | | 380 | | | | | 385 | | | | | 390 | | | | cggccctatc tgtctcctga tgcctgagca gaggtggggg agtccaccct ctccttgatg  1742
cagcttgcgc ctggcgggga ggggtgaaac acttcagaag caccgtgtct gaaccgttgc  1802
ttgtggattt atagtagttc agtcataaaa aaaaaattat aataggctga ttttcttttt  1862
tcttttttt tttaactcga acttttcata actcagggga ttccctgaaa aattacctgc  1922
aggtggaata tttcatggac aaatttttt tctcccctc ccaaatttag ttcctcatca  1982
caaaagaaca aagataaacc agcctcaatc ccggctgctg catttaggtg gagacttctt  2042
cccattccca ccattgttcc tccaccgtcc cacactttag ggggttggta tctcgtgctc  2102
ttctccagag attacaaaaa tgtagcttct caggggaggc aggaagaaag gaaggaagga  2162
aagaaggaag ggaggaccca atctatagga gcagtggact gcttgctggt cgcttacatc  2222
actttactcc ataagcgctt cagtggggtt atcctagtgg ctcttgtgga agtgtgtctt  2282
agttacatca agatgttgaa aatctaccca aaatgcagac agatactaaa aacttctgtt  2342
cagtaagaat catgtcttac tgatctaacc ctaaatccaa ctcatttata cttttatttt  2402
tagttcagtt taaaatgttg ataccttccc tcccaggctc cttaccttgg tcttttccct  2462
gttcatctcc caacatgctg tgctccatag ctggtaggag agggaaggca aaatctttct  2522
tagttttctt tgtcttggcc attttgaatt catttagtta ctgggcataa cttactgctt  2582
tttacaaaag aaacaaacat tgtctgtaca ggtttcatgc tagagctaat gggagatgtg  2642
gccacactga cttccatttt aagctttcta ccttcttttc ctccgaccgt ccccttccct  2702
cacatgccat ccagtgagaa gacctgctcc tcagtcttgt aaatgtatct tgagaggtag  2762
gagcagagcc actatctcca ttgaagctga atggtagac ctgtaattgt gggaaaacta  2822
taaactctct tgttacagcc ccgccacccc ttgctgtgtg tatatatata atactttgtc  2882
cttcatatgt gaaagatcca gtgttggaat tctttggtgt aaataaacgt ttggttttat  2942
ttaaaaaaaa aaaaaaa                                                  2960

<210> SEQ ID NO 4
<211> LENGTH: 22
<212> TYPE: DNA
<213> ORGANISM: Artificial Sequence
<220> FEATURE:
<223> OTHER INFORMATION: PCR Primer

<400> SEQUENCE: 4
ctcagcagta acggccctat ct                                            22

<210> SEQ ID NO 5
<211> LENGTH: 18
<212> TYPE: DNA
<213> ORGANISM: Artificial Sequence
<220> FEATURE:
<223> OTHER INFORMATION: PCR Primer

<400> SEQUENCE: 5
cgcaagctgc atcaagga                                                 18

<210> SEQ ID NO 6

```
<211> LENGTH: 25
<212> TYPE: DNA
<213> ORGANISM: Artificial Sequence
<220> FEATURE:
<223> OTHER INFORMATION: PCR Probe

<400> SEQUENCE: 6
ctcctgatgc ctgagcagag gtggg                                          25

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                 19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                20

<210> SEQ ID NO 10
<211> LENGTH: 1552
<212> TYPE: DNA
<213> ORGANISM: Mus musculus
<220> FEATURE:
<221> NAME/KEY: CDS
<222> LOCATION: (204)...(1379)

<400> SEQUENCE: 10
tggcggccga gcgtgtgtct cctcctccgc cgccgccata ttgtctgtgt gaagctaggg    60
gagcgcggct attgcgctgc cgcttccacc gcagtgtgaa gaaaagggt ctgaaacaaa    120 gtcttaccaa cgtctgcttt tgaacacagt gactgctgga tctttaaaca tcaagttcag   180
ctttgtctgt caacctgtct gac atg tcg gga ccc gtg cca agc agg gcc aga    233
                         Met Ser Gly Pro Val Pro Ser Arg Ala Arg
                          1               5                  10 gtt tac aca gat gtt aac aca cac aga ccc cga gag tac tgg gat tat     281
Val Tyr Thr Asp Val Asn Thr His Arg Pro Arg Glu Tyr Trp Asp Tyr
             15                  20                  25 gaa tca cat gtg gtg gaa tgg gga aat caa gat gac tat cag ctt gtt     329
Glu Ser His Val Val Glu Trp Gly Asn Gln Asp Asp Tyr Gln Leu Val
         30                  35                  40 cga aaa tta ggt agg ggc aaa tac agt gaa gtg ttt gaa gcc atc aac     377
Arg Lys Leu Gly Arg Gly Lys Tyr Ser Glu Val Phe Glu Ala Ile Asn
     45                  50                  55
```

```
atc aca aat aat gaa aaa gtt gtt gtt aaa att ctc aag cca gta aaa     425
Ile Thr Asn Asn Glu Lys Val Val Val Lys Ile Leu Lys Pro Val Lys
    60                  65                  70 aag aag aaa att aag cgt gaa ata aag att ttg gag aat ttg aga ggt     473
Lys Lys Lys Ile Lys Arg Glu Ile Lys Ile Leu Glu Asn Leu Arg Gly
 75                  80                  85                  90 ggg ccc aac atc atc aca ctt gca gac att gta aaa gac cct gtg tca     521
Gly Pro Asn Ile Ile Thr Leu Ala Asp Ile Val Lys Asp Pro Val Ser
                 95                 100                 105 cga acc cct gcc ttg gtt ttt gaa cat gta aac aac aca gac ttc aag     569
Arg Thr Pro Ala Leu Val Phe Glu His Val Asn Asn Thr Asp Phe Lys
            110                 115                 120 caa ttg tac cag acg tta aca gac tat gac att cga ttt tac atg tat     617
Gln Leu Tyr Gln Thr Leu Thr Asp Tyr Asp Ile Arg Phe Tyr Met Tyr
        125                 130                 135 gaa att ctg aaa gcc ctg gat tat tgt cac agc atg ggg att atg cac     665
Glu Ile Leu Lys Ala Leu Asp Tyr Cys His Ser Met Gly Ile Met His
    140                 145                 150 aga gat gtg aaa ccc cat aat gtc atg att gat cat gag cac aga aag     713
Arg Asp Val Lys Pro His Asn Val Met Ile Asp His Glu His Arg Lys
155                 160                 165                 170 ctt cgg cta ata gac tgg ggt tta gct gag ttt tac cat cca ggc caa     761
Leu Arg Leu Ile Asp Trp Gly Leu Ala Glu Phe Tyr His Pro Gly Gln
                175                 180                 185 gag tat aat gtc cga gtt gct tct cga tat ttc aaa ggt cca gag cta     809
Glu Tyr Asn Val Arg Val Ala Ser Arg Tyr Phe Lys Gly Pro Glu Leu
            190                 195                 200 ctt gta gat tat cag atg tac gat tat agt ttg gat atg tgg agc ttg     857
Leu Val Asp Tyr Gln Met Tyr Asp Tyr Ser Leu Asp Met Trp Ser Leu
        205                 210                 215 ggt tgt atg ctg gcc agt atg atc ttc cgg aag gag cca ttt ttc cat     905
Gly Cys Met Leu Ala Ser Met Ile Phe Arg Lys Glu Pro Phe Phe His
    220                 225                 230 gga cat gac aat tat gat cag ttg gtg agg ata gcc aag gtt ctg gga     953
Gly His Asp Asn Tyr Asp Gln Leu Val Arg Ile Ala Lys Val Leu Gly
235                 240                 245                 250 aca gaa gat tta tat gac tat att gac aag tac aac att gaa tta gat    1001
Thr Glu Asp Leu Tyr Asp Tyr Ile Asp Lys Tyr Asn Ile Glu Leu Asp
                255                 260                 265 cca cgt ttc aac gat atc ttg ggc aga cac tcc cgt aag cga tgg gaa    1049
Pro Arg Phe Asn Asp Ile Leu Gly Arg His Ser Arg Lys Arg Trp Glu
            270                 275                 280 cgc ttt gtc cac agt gaa aac cag cat ctt gtc agc cct gag gcc ttg    1097
Arg Phe Val His Ser Glu Asn Gln His Leu Val Ser Pro Glu Ala Leu
        285                 290                 295 gat ttt ctg gac aag ctg ctt cga tat gac cac cag tca cgg ctc act    1145
Asp Phe Leu Asp Lys Leu Leu Arg Tyr Asp His Gln Ser Arg Leu Thr
    300                 305                 310 gca aga gag gcc atg gag cac cct tac ttc tac act gtt gtg aag gac    1193
Ala Arg Glu Ala Met Glu His Pro Tyr Phe Tyr Thr Val Val Lys Asp
315                 320                 325                 330 cag gct cga atg agt tcc act agc atg gca ggg ggc agc aca cct gtc    1241
Gln Ala Arg Met Ser Ser Thr Ser Met Ala Gly Gly Ser Thr Pro Val
                335                 340                 345 agc agc gcc aat atg atg tca ggg att tct tca gtg cca act cct tca    1289
Ser Ser Ala Asn Met Met Ser Gly Ile Ser Ser Val Pro Thr Pro Ser
            350                 355                 360 ccc ctt gga cct ctg gca ggc tca cca gtg att gcc gct gcc aac tca    1337
Pro Leu Gly Pro Leu Ala Gly Ser Pro Val Ile Ala Ala Ala Asn Ser
        365                 370                 375
```

```
ctt ggg ata cct gtt cca gct gct gct tgc gct cag cag taa tgaccccat   1389
Leu Gly Ile Pro Val Pro Ala Ala Ala Cys Ala Gln Gln
    380             385                 390 ctaccttctg atgcctgagc agaggtgggg aagtccaccc tctcctcgat gcagcttgcg   1449
cctgtttggg aggggtgaga acacttcaga agcaccgtgt ctgaaccgtt gcttgtggat   1509
ttagtagttg agtcataaaa aaaaattata ggctgaaaaa aaa                     1552

<210> SEQ ID NO 11
<211> LENGTH: 22
<212> TYPE: DNA
<213> ORGANISM: Artificial Sequence
<220> FEATURE:
<223> OTHER INFORMATION: PCR Primer

<400> SEQUENCE: 11
tccacagtga aaccagcat ct                                              22

<210> SEQ ID NO 12
<211> LENGTH: 22
<212> TYPE: DNA
<213> ORGANISM: Artificial Sequence
<220> FEATURE:
<223> OTHER INFORMATION: PCR Primer

<400> SEQUENCE: 12
ggtggtcata tcgaagcagc tt                                             22

<210> SEQ ID NO 13
<211> LENGTH: 26
<212> TYPE: DNA
<213> ORGANISM: Artificial Sequence
<220> FEATURE:
<223> OTHER INFORMATION: PCR Probe

<400> SEQUENCE: 13
tccagaaaat ccaaggcctc agggct                                         26

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt                                                20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gggtctcgct cctggaagat                                                20

<210> SEQ ID NO 16
<211> LENGTH: 27
<212> TYPE: DNA
<213> ORGANISM: Artificial Sequence
<220> FEATURE:
<223> OTHER INFORMATION: PCR Probe
```

-continued

```
<400> SEQUENCE: 16
aaggccgaga atgggaagct tgtcatc                                           27

<210> SEQ ID NO 17
<211> LENGTH: 2195
<212> TYPE: DNA
<213> ORGANISM: Homo sapiens
<220> FEATURE:
<221> NAME/KEY: CDS
<222> LOCATION: (149)...(1324)

<400> SEQUENCE: 17 agggagagc ggccgccgcc gctgccgctt ccaccacagt ttgaagaaaa caggtctgaa        60
acaaggtctt acccccagct gcttctgaac acagtgactg ccagatctcc aaacatcaag     120
tccagctttg tccgccaacc tgtctgac atg tcg gga ccc gtg cca agc agg       172
                                Met Ser Gly Pro Val Pro Ser Arg
                                  1               5 gcc aga gtt tac aca gat gtt aat aca cac aga cct cga gaa tac tgg       220
Ala Arg Val Tyr Thr Asp Val Asn Thr His Arg Pro Arg Glu Tyr Trp
        10                  15                  20 gat tac gag tca cat gtg gtg gaa tgg gga aat caa gat gac tac cag       268
Asp Tyr Glu Ser His Val Val Glu Trp Gly Asn Gln Asp Asp Tyr Gln
 25                  30                  35                  40 ctg gtt cga aaa tta ggc cga ggt aaa tac agt gaa gta ttt gaa gcc       316
Leu Val Arg Lys Leu Gly Arg Gly Lys Tyr Ser Glu Val Phe Glu Ala
                 45                  50                  55 atc aac atc aca aat aat gaa aaa gtt gtt gtt aaa att ctc aag cca       364
Ile Asn Ile Thr Asn Asn Glu Lys Val Val Val Lys Ile Leu Lys Pro
             60                  65                  70 gta aaa aag aag aaa att aag cgt gaa ata aag att ttg gag aat ttg       412
Val Lys Lys Lys Lys Ile Lys Arg Glu Ile Lys Ile Leu Glu Asn Leu
         75                  80                  85 aga gga ggt ccc aac atc atc aca ctg gca gac att gta aaa gac cct       460
Arg Gly Gly Pro Asn Ile Ile Thr Leu Ala Asp Ile Val Lys Asp Pro
     90                  95                 100 gtg tca cga acc ccc gcc ttg gtt ttt gaa cac gta aac aac aca gac       508
Val Ser Arg Thr Pro Ala Leu Val Phe Glu His Val Asn Asn Thr Asp
105                 110                 115                 120 ttc aag caa ttg tac cag acg tta aca gac tat gat att cga ttt tac       556
Phe Lys Gln Leu Tyr Gln Thr Leu Thr Asp Tyr Asp Ile Arg Phe Tyr
                125                 130                 135 atg tat gag att ctg aag gcc ctg gat tat tgt cac agc atg gga att       604
Met Tyr Glu Ile Leu Lys Ala Leu Asp Tyr Cys His Ser Met Gly Ile
            140                 145                 150 atg cac aga gat gtc aag ccc cat aat gtc atg att gat cat gag cac       652
Met His Arg Asp Val Lys Pro His Asn Val Met Ile Asp His Glu His
        155                 160                 165 aga aag cta cga cta ata gac tgg ggt ttg gct gag ttt tat cat cct       700
Arg Lys Leu Arg Leu Ile Asp Trp Gly Leu Ala Glu Phe Tyr His Pro
    170                 175                 180 ggc caa gaa tat aat gtc cga gtt gct tcc cga tac ttc aaa ggt cct       748
Gly Gln Glu Tyr Asn Val Arg Val Ala Ser Arg Tyr Phe Lys Gly Pro
185                 190                 195                 200 gag cta ctt gta gac tat cag atg tac gat tat agt ttg gat atg tgg       796
Glu Leu Leu Val Asp Tyr Gln Met Tyr Asp Tyr Ser Leu Asp Met Trp
                205                 210                 215 agt ttg ggt tgt atg ctg gca agt atg atc ttt cgg aag gag cca ttt       844
Ser Leu Gly Cys Met Leu Ala Ser Met Ile Phe Arg Lys Glu Pro Phe
            220                 225                 230
```

| | | | | | | | | | | | | | | | | |
|---|---|---|---|---|---|---|---|---|---|---|---|---|---|---|---|---|
| ttc | cat | gga | cat | gac | aat | tat | gat | cag | ttg | gtg | agg | ata | gcc | aag | gtt | 892 |
| Phe | His | Gly | His | Asp | Asn | Tyr | Asp | Gln | Leu | Val | Arg | Ile | Ala | Lys | Val | |
| | | 235 | | | | 240 | | | | 245 | | | | | | |
| ctg | ggg | aca | gaa | gat | tta | tat | gac | tat | att | gac | aaa | tac | aac | att | gaa | 940 |
| Leu | Gly | Thr | Glu | Asp | Leu | Tyr | Asp | Tyr | Ile | Asp | Lys | Tyr | Asn | Ile | Glu | |
| | 250 | | | | | 255 | | | | | 260 | | | | | |
| tta | gat | cca | cgt | ttc | aat | gat | atc | ttg | ggc | aga | cac | tct | cga | aag | cga | 988 |
| Leu | Asp | Pro | Arg | Phe | Asn | Asp | Ile | Leu | Gly | Arg | His | Ser | Arg | Lys | Arg | |
| 265 | | | | | 270 | | | | | 275 | | | | | 280 | |
| tgg | gaa | cgc | ttt | gtc | cac | agt | gaa | aat | cag | cac | ctt | gtc | agc | cct | gag | 1036 |
| Trp | Glu | Arg | Phe | Val | His | Ser | Glu | Asn | Gln | His | Leu | Val | Ser | Pro | Glu | |
| | | | | 285 | | | | | 290 | | | | | 295 | | |
| gcc | ttg | gat | ttc | ctg | gac | aaa | ctg | ctg | cga | tat | gac | cac | cag | tca | cgg | 1084 |
| Ala | Leu | Asp | Phe | Leu | Asp | Lys | Leu | Leu | Arg | Tyr | Asp | His | Gln | Ser | Arg | |
| | | | 300 | | | | | 305 | | | | | 310 | | | |
| ctt | act | gca | aga | gag | gca | atg | gag | cac | ccc | tat | ttc | tac | act | gtt | gtg | 1132 |
| Leu | Thr | Ala | Arg | Glu | Ala | Met | Glu | His | Pro | Tyr | Phe | Tyr | Thr | Val | Val | |
| | | 315 | | | | | 320 | | | | | 325 | | | | |
| aag | gac | cag | gct | cga | atg | ggt | tca | tct | agc | atg | cca | ggg | ggc | agt | acg | 1180 |
| Lys | Asp | Gln | Ala | Arg | Met | Gly | Ser | Ser | Ser | Met | Pro | Gly | Gly | Ser | Thr | |
| | 330 | | | | | 335 | | | | | 340 | | | | | |
| ccc | gtc | agc | agc | gcc | aat | atg | atg | tca | ggg | att | tct | tca | gtg | cca | acc | 1228 |
| Pro | Val | Ser | Ser | Ala | Asn | Met | Met | Ser | Gly | Ile | Ser | Ser | Val | Pro | Thr | |
| 345 | | | | | 350 | | | | | 355 | | | | | 360 | |
| cct | tca | ccc | ctt | gga | cct | ctg | gca | ggc | tca | cca | gtg | att | gct | gct | gcc | 1276 |
| Pro | Ser | Pro | Leu | Gly | Pro | Leu | Ala | Gly | Ser | Pro | Val | Ile | Ala | Ala | Ala | |
| | | | | 365 | | | | | 370 | | | | | 375 | | |
| aac | ccc | ctt | ggg | atg | cct | gtt | cca | gct | gcc | gct | ggc | gct | cag | cag | taa | 1324 |
| Asn | Pro | Leu | Gly | Met | Pro | Val | Pro | Ala | Ala | Ala | Gly | Ala | Gln | Gln | | |
| | | | 380 | | | | | 385 | | | | | 390 | | | |

| | |
|---|---|
| cggccctatc tgtctcctga tgcctgagca gaggtggggg agtccaccct ctccttgatg | 1384 |
| cagcttgcgc ctggcgggga ggggtgaaac acttcagaag caccgtgtct gaaccgttgc | 1444 |
| ttgtggattt atagtagttc agtcataaaa aaaaaattat aataggctga ttttcttttt | 1504 |
| tctttttttt tttaactcga acttttcata actcagggga ttccctgaaa aattacctgc | 1564 |
| aggtggaata tttcatggac aaattttttt ttctcccctc ccaaatttag ttcctcatca | 1624 |
| caaaagaaca aagataaacc agcctcaatc ccggctgctg catttaggtg gagacttctt | 1684 |
| cccattccca ccattgttcc tccaccgtcc cacactttag ggggttggta tctcgtgctc | 1744 |
| ttctccagag attacaaaaa tgtagcttct caggggaggc aggaagaaag gaaggaagga | 1804 |
| aagaaggaag ggaggaccca atctatagga gcagtggact gcttgctggt cgcttacatc | 1864 |
| actttactcc ataagcgctt cagtgggtt atcctagtgg ctcttgtgga agtgtgtctc | 1924 |
| agttacatca agatgttgaa aatctaccca aaatgcagac agatactaaa aacttctgtt | 1984 |
| cagtaagaat catgtcttac tgatctaacc ctaaatccaa ctcatttata cttttatttt | 2044 |
| tagttcagtt taaaatgttg ataccttccc tcccaggctc cttaccttgg tcttttccct | 2104 |
| gttcatctcc caacatgctg tgctccatag ctggtaggag agggaaggca aaatctttct | 2164 |
| tagtttttctt tgtcttggcc attttgaatt c | 2195 |

<210> SEQ ID NO 18
<211> LENGTH: 63000
<212> TYPE: DNA
<213> ORGANISM: Homo sapiens
<220> FEATURE:

<400> SEQUENCE: 18

-continued

```
catcagatgg agccctgtcc actgggggct cccagtctga tggaggagac agactgaggt      60
cctcaggtta ctgactgata gtgtctgggt tggagggagt taaacagaga ggagacccct     120
agaggaaagg atccctgaat tagttcaatc ggcatacaga aattatccag tccatgaggt     180
gacagtaaga gaagtaactg ccagtgtaaa gggagggagg caacacagct aagttccagg     240
aattgtttgc agtcttgtgg gtggaatctt ccggaatttg agaagagagt ggcagaatag     300
gaggctggaa aggagggttt ggccaaatta tggaggactc tgaatgtcaa gtgaagagtt     360
tgggctatct ttggtgcata aagaggtcca tgggagattt tgaccatag ggagaccatg      420
atgagctctg catggtagaa agtgctttgt ggctgttttg gggaggtagc tcgggcaagg     480
agagcagggg tgggaggcag atagaaggaa aaaaaaacac tgtattttgg acgcacagct     540
cttggcagga ctcctgtagg aggaaggaat tgggccttgg tctcttgaga gctagtatcc     600
tcacttctca gactcctgcg ccatgcccct cctagggtcc aactttcatt cacttcttcc     660
gaactccaag tttgaataga aagtgttgct gaaaccctaa tttaaaacga ggggtcagag     720
caaaagagac ttcagctccc agaatgcttg gctctacagc tctgcaggtc gcgcatggtt     780
ctttttcaaga aaggggggcc agctgggtga agtgtgggaa acctgggtac cgccatctta    840
acttgggtca aaccaactgt tcacctaatg ggaggttcgt gttctctctg ttgtcacttg     900
ttaacactat tgaaataaaa tgcgcttaac tattgcaagt ctccttattc tgctttgcgt     960
tggggattcc ttccattttg caccctaggc cagaactgaa tccctaaggt tacaatagga    1020
catcccagca tggccgcatt cagagagatt cctctggggg cggagtcgga agctgtctcg    1080
ccccgcctcc tggtaggagg gggtttccgc ttccggcagc agcggctgca gcctcgctct    1140
ggtccctgcg gctggcggcc gagccgtgtg tctcctcctc catcgccgcc atattgtctg    1200
tgtgagcaga ggggagagcg gccgccgccg ctgccgcttc caccacaggt acctagggag    1260
cagccaggcg aggtcgttgg cgggtgggt gggcccagga tagggcagcg gagcgcggcc     1320
gaccctcacg cttccagcag actcctgagc ggcccgtcgc cttcccctgc ccccaccttc    1380
acacataaac caagcgaggc ccctgcagcc catcggggag gcccagggc cacccctcag     1440
ggcggagggc gaggtttggg ggcagaggcc gatgtgaggg tgggaaccgg ctgccggagt    1500
ccagcttatt gcagaggaga ggactgaact gggtgggac tagggacaa cttgaggag      1560
ggggtcgtca gagggggaag ggaacttgag gggtgggcc gcagggggt gctggggag      1620
ggtgcgagg gagtggtgcc tgctgggtag tgtgcagtga accctcccgc gaaactgggc    1680
agctggagta ggggccttct tagggtccct ctgggcgggg ctgagcttcc cacctgcaga    1740
gtgggtgcga ggtggagaga accccaggcg gggttgctgg ggcgaagggg gaagggacc     1800
aagacgtggg gcagaacgtc tggagttgga gttaaggact agttaggagc ctggatagaa    1860
aaagaggtat ggagagaaag cttggctaag ggtatacata tgttggtgac cttttgaaag    1920
agtaggactt ttcaattttg ttttttcgttg tgtgttttttt gcagtgttgg aacattgcta    1980
gattaagcag gtgatgggtg gagcttctgt agtttgtttt ggggaagcag agtcagggtc     2040
aggagaagtt gcatcttggc tattgctttg tgtggaggaa agagttttga aaagaaggtg    2100
gcaaattatt tgggaagact tgattacttt tcagctgttt aattctacga gaatgggaca    2160
tggggagagg aaatgaaaac taagaagaga ggccgggcgt gtggctcacg cctgtaatcc    2220
cagcactctg ggaggccgag gcgggtggat cacgaggtca ggagttcgag accagcctga    2280
ccaacacggt gaaaccccgt ctgtactaaa aatgcaaata tcagccgggc ttggtggcgc    2340
gcgcctgtaa tcccagctac tcgggaggct aaggcaggag aatcgcttga acctgggagg    2400
```

```
cggaggtggc agtgagctga gatccgccac tgcactccag cctgggcgac agagcgagac  2460
tccgcctcaa aaagaaaaaa gaaaactaag aagggaagat ttttccaaga attggagact  2520
tcattccatc tgaggagtgc agtgtaggcc cagtggttaa aaaccagact gcctaggttc  2580
tcaaatatca gggccattgc tacttagctg tgtgacctaa actctctaag cctcagtttt  2640
cccgtctgta aaggggggat gatggtattt tctagcttgt gagtttacgg agaagagtaa  2700
ataagacaat ttgtgtcaag tgcttactac agtgtctggc aggtagtaag tgtagtaagt  2760
agcttttacc tgtcactgta aagggactag ctggtatatt tggggctctt ctgttctaag  2820
taaaatttat agtcaagaat ttgactgtag acagggcttt agagtagtat ctttgtagtt  2880
gttgtagggt tttgttgtaa gtcatttggc tttactggct tggtggacct ggggctgaaa  2940
gtccagtacc aatactagtt ctcctccgtg gtattctcaa agttcacct gcagtcttag  3000 cagggcatgt ttttgtcctt ctgtgacttt gaaatacttg gctttggttt gctattgcgg  3060
gagggtgtat gacttgaaga aagaatgcaa gattggaaat ttgcttagat tgattaatca  3120
actgattata cagttaggtc cccgtgaggt gacttttctt taaaaataaa aaaaagccta  3180
gttatgtact cctttgtgga atacagagaa gagaaataca catttaagga ggagcatggg  3240
ttagtttcta agtagttatg ggtgaagtgc cttgcaattt gaggatgaaa caggtggcaa  3300
ctccttttcc atactgcgcg tccttttcct actcactcat ccagagtgag tccttgtttt  3360
tactattgtc tctatctctg aacatacatc tttgtgtcac ataagtaaag acatatgtat  3420
gtatgtatat atactttact tcacataagt aaaatatata catctttact tcacactctg  3480
ttaaagaaag ggatgatttt ctttaggaag tgagtttaaa cccttccata ggacttggat  3540
ttgtagtagg cagaattaca tctccctctt cccaaggtgc cataccttga tccccagaat  3600
ctgtagctat cctgtgttac atggcaaaag gaacttggca ggtgtaatta aggttaagaa  3660
tcttaaaata gaaaaattat cctggatttt ctgggtgggc cgaatctagt cacttaagtc  3720
cttaaaagca gagaactttc tccaactggg atcagagaaa tgggcagaaa aggaaatcag  3780
agatttgaag catgagaagg actccatttg cctttgctag agaggaccac atggaaagtt  3840
tatcagaagg aatgtgggca gcctctagtg gcaaagacca gtccctggct gacaaccaga  3900
aagaaatggg gacctcagtt gtgcaaccag aaggaacctg aatttggtca acaacctgat  3960
tgagcttgga agtgaatttc ccagtttcca ccaaggaatg caaccttgag acaccttgat  4020
ttttggcctc gtgagaccct aagcaaaaga cctagctagc caagcccacc caacttctga  4080
cctacaataa ctgtgagata acaaatttgt gttattttta gctactacat ttgtggtaat  4140
ttgttatggc agcagtagaa cactagtata gattttggta ccaggagtgg ggtactatta  4200
cctaaaaatg aaagtggcag tagataaagg ttagaattgt tttgaggggc atgatagaaa  4260
aggcctggaa cacaggagga tcgcttgagc ccaggaagtc aaggctgcag tgagcggtaa  4320
tggcaccact gcactccagc ctgggtggca gagtgagacc ctgtcaaaaa agaaaaggcc  4380
taggacatac ttttagtagc aatatggatg ttaatgactc tgctagtgag gcccagaca  4440 gaagtgaggt ctttcttatt ggaaactggc agaaggggga tccttgttac atagtagcaa  4500
ctaagtttag cagaattgta tcctatggtt atatggaaag ccaaatttgc aagtgatgaa  4560
cttgtatatt tagctgagat ttccaagcaa agtattaaat gtgcagcctg gtttatttgt  4620
gaatgtgaac tttaatggag tggacccatg tggaatactt ccacagccca ttaggttctt  4680
gagaatttta tgccaacata aacagttcta gtttggattg aaagagacag aaagtaatag  4740
```

-continued

```
ggctgttgga cccccaaat tctactgata ggaagcaggc tgataaaact actcacatgt    4800
gaatgtgttg cttttcataa aagaatcagg gtgactcaga cggagatagg agagcccaga    4860
ggggtggagc taaaagctgg agaggatttt tcccaggctt tgaaatggaa tggagattcc    4920
ctagattttg aaactgcttt ggaccggagg ctctgttttc ttttacattt tgcccatttg    4980
aactggaatg tctaactgtt attctctaca tgtctcacag tggtatgttg ggagtagaga    5040
acttgtttct ttaggaattg tgcccagga attggactta ctgttttgtc cccagaacct    5100
catccacacc tgaatagatg aatgagattt gggacttctg aaatgataag ctttagatgg    5160
gaaacctttg ggaccttggg atgggatgga tgtattttgc atttgagaga gagatgaatc    5220
cttggaaacc agaaggcaga ctgcggtaag cagaatggct cccctacgat ttccatacta    5280
taaaccctgg aacatgaata tgttaagtag atttaattaa agttaaggat cttaggtaga    5340
ttatcttgga ttttctgggt gggtttattc tactcacata agcacttaaa agcagagaac    5400
tttttctggc tggtgtcaga gatgaggcag aaggggaagt caaatttgaa gcatgagaag    5460
gactcagcct gccgttactg gaggggacca gattgaaagt gtgagacggg gaatgcaggc    5520
agcctctagt aggaaaggcc agtcccagct gacaaccagc aaggaagtgg gaactcagtc    5580
ctacagctgc aaggaactaa attcagccaa tagcttgaat gaatgtggaa gcaaattttc    5640
cccagagttt ccagcaggga acccacccac tggatacccc catttagccc ttgtgagacc    5700
cagtcaagcc cactgacttc tgtaagataa tccatttgtg ttgttttgtt tgtgataatt    5760
tgttatgaca caatggaaaa caaatacagg ggttttgctg gttttatttt agagtctttg    5820
ggatatcatt ttctagagaa caaagatagc aaagattcta taaacaatt tagtcctgga    5880 agactccacg gaataatggt gttgagtgga acctgtgcct gtttcttgat gtttgaatat    5940
tattattgtc cttagatgca gtttgaaggg gcttgatggt cagcttagtg agatgtagtt    6000
tctgaaggtc taggacattg gtaggatttc tgtaaatagg tggttcttcc atatcttgga    6060
taaatgacat aatttcttca ttagttttta ttggcttaat aatgggtttc tatgacagcc    6120
ttttaaggct tatttcatat tttttttagag gagatgaaa tgggtgatac attttgtga     6180 atttgtaact gtctctctgt tctctcacac ctcccacccc accccagctc agctcaaact    6240
tgtaagatct tttctccctg tcattgtctg ttgaggttgt tgagtttaag agtcagatct    6300
gggaatcatc actacagaat ggagtttcta gcttttaaga aaagtctttt cttttgttc    6360 tttaaagtat cctattaatt ggattcataa aatatggact aactaaactt tagtcagagg    6420
atgaaggaag tgagaccatt tcttttgagt tattacctga atagaaagat gattacaaga    6480
ttagcatttc agggtatgaa agactttaga ggttatgttt gactttgggt ttagagtaag    6540
ggaaattggg ccacatgaat gttaactggt ctactaagat atctcagccc tagagctagt    6600
ctagaatcct ggtccagcca atagagaatc atgacttttg aactatgttc cctgagtacc    6660
cttttctact gttggccggg catggtggct cacacctgta atcccagttc tttgagaggc    6720
cgaggtgggc agatgacttg aggtcaggac aagaccagcc tggccaacat ggtaaaaccc    6780
catctctact aaaattagct gagtgtggag gtgcgtgcct gtggtcccag ctactcagga    6840
ggctgagaat cacttgaacc tgggagacgg aggttggttg cagtgagtca agatcacgcc    6900
actgcactcc agcctggggg acagagcaag actccgtctc aaaaaaaaaa aaaaagatg    6960 ttaactgtct ataatattca actatatgac aactttgca taaatattac agtatgattt     7020
gtacaagttc agaaactgaa aaccaatatg atttgccatt gaattaggta agggcttagt    7080
attttaaggt aataaataat gtgatacttg atttgaaatg agaaactggg ttttgatctg    7140
```

```
tcacaattcg tgggtaacct ggataaggtt tgtttcatga gagtattaat gtgttcttat   7200
acctgaattt ctttgaactt ctgaaatgga taatttcgaa agtagcatgt catttagttt   7260
atagagaaat ctaggccagc cagcttttca atgaagaaa  ttcctctagg attattaagg   7320
aaaagtagct gctgtcattg taacaaagga tgtattttca ttgggttata gacaattggt   7380
agttttctta cgttgagtgc tcccagatgt actttttttt tttcacatgt agaagtcaaa   7440
gattgagtct tttaaaaagt ttaaggtgaa agcattcaca gtatcacaag atactgctaa   7500
gagtggcatt ttaactggtt tctacaaatt ctgtctttca gtcttagaca ttaaaaaacc   7560
ctacgtagca acagttgcta tggtcggcaa gcttctttac attcgtggtg ataatgtttt   7620
cttgcataga aaatattgtg ttatctgagg tgacagtttt agggttaaat accaaggtac   7680
aagttagatt aatgttttat aattttttat gtgtgacatc ttaaatgccc ttatattggc   7740
tgctcttttc ttttatact  ttcttgtctt gtgggttttt ctgacaggtt tttattagct   7800
gaaacatttt aatttgcttg gaaaagtgaa catttgaaat tttcctgaag ttatgactaa   7860
tgctttaatg ggcatttctc agtttagcta tctcatcaat gttctataaa ttttaagaaa   7920
gctaccctgt ttaaaatgaa tgggtaaatt attttccaaa aaatggtatc atgtcatatc   7980
cagaaatacg agatggtcat tttgggttat tgaattcata accactcaga agatgttgtt   8040
cattcagcag atcctgagcg cctgccacgt ttctggcagg cgttgtgcta agatctcca   8100 aactgtcact gccctccaag ctcaaaattg agtgacgttt tctgataaca ggcatatcat   8160
accacaactt agtagatttt ggaggtgttt tcttataata actcctattt gctttgtatc   8220
ttaggtgtag ttttttgaaac agctgcagaa atgagaaggg ggtagaatag agaattaatt   8280
gagattgcgg gtagggaggg gaaggcaata ggttagtggg aaagaactcc cactttgagt   8340
ttggggaagt ttacttaacc tcttcaagtc tgggagttct tgtctctaca gttcggataa   8400
caactacctt gggcaactta ctaactttg  gtttcttcac ctgtaacatg ggaattagta   8460
gtacctacct caggattttt gtgaggatta ataactagag tactagctag tattatctca   8520
ggattattga ggattaaagg agaaaattga taaaatgtct ggcatgtggg tgcccaacat   8580
tagttctttc ccttcccttt cggagaaaag aatgtgttta ttgccagtgc tgtcattctt   8640 cattcttat  tttcattttc tgctgccaag agttcttatt tttttaatga acttttgac    8700 ctgtacttcc ttgtttctaa tgtagcctgt tgggtgggtg aggtatgaat tgctgcctag   8760
gggtggatca gtatgtaagt cacgcccagt gtagattacc tcaattactc gtgtacagtg   8820
tctattacct agtcctggtg agtctaggat tcttttgctt ctagatagag aaggtaatat   8880
tcccatctca gactcaggaa aaggtctacc tttgctcacc tatagacttg taaatataga   8940
tcagaggtct tactcccagt ggttctctga tcacagtttg ggaattgctt gaatattgtg   9000
tgttagggat atgtttggag aaggccagct ccctgcatta acatcttctc tatgtcttgc   9060
tctctcaggt aatccactaa cttgctttct tgtttgcttt gtattattaa gtgataaact   9120
gtaggcagac caggaacttg tatttatcgg cactttaaaa ctttttttt  ttttttttt    9180 gagatggagt cttgctctgt cgcccaagct ggagtgcagt ggcgcaatct ctgcctcctg   9240
ggttcaagtg attctcctct ctcagcctcc taagtaactg ggattacagg tgcatgccac   9300
cccaccgggc taatttttgt attttagta gaggcgggt gtcgccatgt tggccacgct     9360
ggcctcaaac tcctgacctc aggtgatcca cccgcctcag cctcccaaag tgctgggtt   9420 acaggcgtga gccaccgcgc ccggccagtg ttttgtgtat ttatgattat atagaatggc   9480
```

-continued

```
tacaaatggc catctgcttt ggagttgtct acctttttgtg aaaaaatgaa aatagactat  9540
tgcctagcaa ttaagtattc aagcatgtat tttgccacat aatttattgt gagaaggtta  9600
tcaatgtcaa ataaaatgct ttcattattt gcttctattt gtctgtcttc ctgaccagtt  9660 cattttttcct tccagtgaag ccatcttgag ctagggtttt ctttgtgggt agttgttaat  9720 ttttttttgta gagacaaggt ctcaccatgt tgcccaggct ggtctcaaac tcctgggctc  9780
aagcagtcct cttaactcag cctcccaaag tgctgagatt acactcatga gccaccacac  9840
tggtccgaag aaattttttt tttttttttt tttttttttt tttttgggag atagcatctc  9900
actctgttgc caggctggag tgcagtggca cgaccttggc tcactgcaac ctccacctcc  9960
cgggttcaag caattctcct gcctcagcct cccaagtagc tgggactaca ggcgcacgct 10020
gccacgcctg gcttttttttt tttttgtat tttagtagag atggggtttc actgtgtttc 10080
ccaggctggt ctctaacacc tgagctcagg caatccaccc atctcggcct cccaaagtgc 10140
tgggattgca ggtgtgagcc actgcaccca gcctggtctg aagaatttttt aaacaccaca 10200 gctaaggacc tgagcattca tctgcagcta cctatatgct cttgttacat acagttgtta 10260
tactaggggg ttttttcacag ccatctttta tgactgtttt tggaaaacat cacattgacc 10320
ttcatacata ttcaaaactt taggctttgt tgcatctgga gtccaacact gaggcccaca 10380
gatgtcacca gcccccagcc agcaaggtgg ggcatgtctc agttgtcttc ctttctccct 10440
tcagtagcca cacagaaaag cttttccatc atttaaaatc tgattttttat acaattgtgg 10500 cctggtggcc agcccattca ggtaaaagaa taatgaagaa acctgattat tgaaactcag 10560
tatcccaccc ctaccttgcc tccaaattta aagcagttca ttttattata gtgttttgga 10620
taggctgtta ataaatcagt ttggagaact aaggaaatag tattaaattt agtgaaagaa 10680
acctatttag gctttggatc ctaaacagat ctggcttcca ccacttagta atcctgttgt 10740
ttttggcaga ttatttaacc tctgaatctg tttatttcta aaatcagaat atgcatctga 10800
tactgtgcct ggtttgtaag aggcattcaa atggtaacag tagttattac attcataagt 10860
gctgaatttt tctttagatt actgtatatc ccaaatgaag ttttccatct tttggttcca 10920
gagggtaata gccagtggag taaagtttca cattgtgact ttattttgct tatatggcgt 10980
ggtaaaaagg tgtatagatg atgactatat tgtaagagac agtactggaa ttccgatttc 11040
tcttaggtgt ttggggtaga actattaatc caaatcaaac tgcttggatt ttcttctaat 11100
acctcccttc attgggagac ctcacactgt tgctatgtca tttatgtcac attgacactc 11160
agatcccttt tctgggttga aggtggagaa atgtaattca cacaaaaggc ccaaatgcta 11220
atgttttctg ttttactgta cttcctggtt tgttttatgg aagtaatact tccgtgtatt 11280
ggtttaattt ttttgtatgt atgtatgtat ttattttgag acagcgtctc gctctgtcac 11340
ccaggctgga gtgcagtgac atgatctcgg ctcattgcaa cctctgcctc ctgggttcaa 11400
gtgatgcttc tgcctcagcc tcccaagtag ctgggactac aggtgtgtgc caccacacct 11460
ggcctatgtg cattgttttt aaaaacaaac atgttgtatg ttttgtatgt aggaataaaa 11520
gcagaaggcc cctaggggca tgttaggatt tataatctcc taaagttaaa tattctgcaa 11580
gtttacacaa gcagtaactt catgaattac taagtattac tgagagtatt tatgttccaa 11640
attcgaagcc ttaatcaaac cagaaaaaaa catattctgt tgggtttgaa caggtagttt 11700
tcttattcat tgtatactta gaaccttggg acttaaaggt cagagagtca agggaactgc 11760
caaggagtta gttgctagat attttttttgt tttttttgagc tgtatatatt tccccacttg 11820
aaaaaacaaa aacactacta cttatatggc attagtatga taggtgagag agaatgttgt 11880
```

-continued

```
tggccatggt taccaccta aattgacatg ggaaaagaga atcaatatga agtggaggaa    11940
aaaaaacaat aacttcattt aatcatacat ttttaccgtt aacctgtttt cttttggctt    12000
atccttctga gctagggtaa ggaggcttgt tttgtctttg ttgtttttgt ttttttgtgt    12060
cagtgacctc caaatagatg atcttccaga cgaaatggtt gcctgttagt acatctggtc    12120
tatacttgaa agctgcaaaa ggtgattgcg tatctcttga aataagagga attgtgaaat    12180
agttttctca acctgctgca tggattttga ctattcaggt cgtgatctcc acaagttatt    12240
taaactagaa tttctcaacc agtgtattgt gttagggtgc gttacagatg tgttgagata    12300
ctggtcccct cacacctctg gccattcatg cagaatatag tttggataca gcatccaaac    12360
taatgacctc agatccagag cagtcttgat catttacccc attgtgccat acaaatatta    12420
ttttctgtct tgactgtaaa aaagactggg agcagtggct cacacctgta atcccagcac    12480
tttgggaggc cgaggcgggc agatcacaag atcaggagtt caagaccatc ctggccaaca    12540
tggtgaaacc ctgtctctac taaaatacaa aaaaaaaaa aaaaaaaat tagccgggca    12600 tggtggcgct tgcctgtagt ccagatactc aggaggctga ggcgggggaa tcgcttgaac    12660
ccaggaggcg gaggttgcag taagccgaga gcgtgccact gcactccagg cctggcgaca    12720
gagcgagact ccatctcaaa aaaaaaaaa gttaaaagtt tagaaaaact gggagcacta    12780
atttagaaag ctcagtaatt ggatatctga acagttttaa gattcaaggg ggtaaacaat    12840
ctgaaaataa tcttggtttt aagttttttaa agccatttta aggtacctct ctgacccaca    12900
agtaattctc tttggacaca tgattcaaag gatatgcttt aaaatacaag actgtgaaca    12960
atttaaggtt ggacagtagt gaagaaattc aagttcttat tttctaagca gtaatgtgag    13020
gcagaagtaa agttcccttt tgtaaaactg ttatctctac ctgactaact ctgaatgcta    13080
ctgtatcttt tctgaggctg acatttttgtt aatcattcat caagcttggg tctcatactc    13140
tgaagcctag gatacattgt cttcttgtct tccttcagga aagaatggca tatacttagt    13200
ttgagcagtt taattttta atatttatgt aaatcaccaa gttagccttc ttagatgagt    13260
ttctgtttgt ctaactcagg aattattaat tttgctggag tttacagatt tcctgagcct    13320
gtaataattt ttttcttcaa aaaaaaatgt acatgtacat gctgctttat atacatttac    13380
cagagagttc atggccactg atctcattgt tgagctgcat tttcagttcc aaaatttgtg    13440
tagtctaaat aagagttccc ccatcttatt atttgtaaat ttatatattt agtataaacc    13500
agggattgat tgctcaaatg ccttcaggag tcgagtcaat aaggtaaatg aagagttgtc    13560
caggtttacg tgtggtatct ccattgggtg tctgttaaaa gagccagttg ttggacagtc    13620
acagcttagc atatccagca ggtttttgtc agtgcaggaa tgaagagtca ttgttaccag    13680
acagacagac ctacctgccc tccctcctgc tttatttctt ttaagaaata gaaagttaaa    13740 tttttttta attttggtaa ctgtcacttt gaaaatatt aattgtgaaa attttaata    13800 cataattcac cttaataccct tttcttttgt ttttgagac ggaatttcac tcttttcacc    13860
caggctggag tgcaatggcg cgatctcagc tcactgtaac ctctgcctcc caggttcaag    13920
tgattctcct gtctcaggct cccaagtagc tgagattaca ggtgcccacc accacacctg    13980
gctaattttg tatttttagt acaaatgggg tttcatcatg ttggccaagg ctgtcatgaa    14040
ctcctgacct caggtaatcc gcctgcctca gcctcccaaa ctggtggggt tacaggtgtg    14100
agccactatg cctggcccct gatttacttt ttaaaaacag tgtgaaggct gggcactgtg    14160
gctcatactg tagtcccaac actttggaag gctaagatgg gatgatcgct tgaatccagg    14220
```

```
agttcgagac cagcctgggc aacatggcga aaccctgtct ctactaaaaa tgcagaaaat 14280
taactgggcg tggtggcgca cacccatagt cccagctact tggaagactg aggtaggagg 14340
atcacttgag ctcaggagtg tgaggctgca gtgaagtgaa ctatgatcat gccattgcac 14400
tccagcctgg gtgacagagc aaggtcctga ctctaaaaaa aaaaaaaaaa aggaaaaaaa 14460
gtgaaaaact tgtacacata tgcacctagc gacattattt catagtagcc aaaaagtgga 14520
gacagtccaa atatctgtca gtgaatggac aaccagaatg tgatgtattt atacagtgaa 14580
ttcagctgta aaaggaaatg aattactgat acttgcaaca acgtggataa acttgtagac 14640
attttgctaa gtggaagagg ccacatattg catgattcca tttatgtgaa atgtccataa 14700
taggcaaata catgaagaca gaaagcagat tattggttgc cagaggattg taggaagagg 14760
ctattgggag ttaatcctct gaggtactgg gtttcttttt ggggcgatga agtgttctgg 14820
aatcagatag tggtgatggt tccacagcat tgtaatata cgaaaacaca ccatttagg 14880 gtactgattg taccctaaaa tgatgagttt tatgttacat ggattttatc tcaatttta 14940 aaagtaatat gtgagccaaa taggagatat acacacagag tagtcctgtt cccagccatc 15000
tgtgggaaat atattccaag atccccagtg gatgcctgaa accacagata ataccaaacc 15060
tgattatcat cagttggaac acagtttct gttgatgtct tctacccaca aatttaatgc 15120
cttttccatt ttaactaagc atttatcaca tactgcggtc ataacttttg cagtttgagg 15180
tacaacagca aaacaaatgt gaatttattt ttccctcttc acattatcac tgatagaaga 15240
tttgttctta ccatagatct tagcaatttc cacatatgat ttttttttcc atattaagtc 15300
aagaactttt acctttttac ttaaaggaag cactttacag cttcacattg gcatttccag 15360
attctcagca tcgctactct tgcactttgg ggcatttctt aagtaaaata agggtaactt 15420
gaagacaagc actgcaatac tgcaacattc aagtaaccaa gaaggctacc aagtgactaa 15480
tgagcaggtg gcatatacag ctggacaaag ggatgattca catccagggc tggatggtac 15540
tagatggtgc aagatttcat cacattactc agaaccatgt acaatttaaa acatggctgg 15600
gtgcaatggc tcatgcctgt aatcccagca ctttgggagg gtaaggcggg aggattgctt 15660
gagcccagga gttcaagact agcccgggca acatagtgag aaaccttctt tacaaaaaaa 15720
aaaaaaaaat agccaggagt ggtggtgcat gcccgtggtc ccagctacaa gggaggctga 15780
gatgggaggt agaggctgct acagtgagct acggttgcac cactgcactc cagcctgggt 15840
gactgagtga atcctcgtct ctaaaaacaa acatggaaaa taaaacttat gacttatta 15900 tttctggaat tttccattta atattttcag actgcagttg actgcgggta actgaaacca 15960
tgggtatggg ggttggctgt gtttgtggtc accagtttac agtcccttgc tgtagaacag 16020
aagaataggc tgtgaatcta gacgaatgtt ttccaatcac tacctctgac attgggaagg 16080
ttatgcagtt ttgccttctg taaaatgaga agacattac ttaggtcatg gacttgctgg 16140
tttaacagtg ataaatctgg ctgggcatgg tggctcatgc ctataatccc agcacgttgg 16200
gaggccaagg taggaggatt gcttgagctt aggacttcca gaccagcctg gtaacataa 16260 caagacctca gaacaaaaac aaaagacatc tcagaaaaaa aaacaaaaga aagaaagaaa 16320
aaaaagaaaa aatttaatta gcaggggaca gtagtgtatg cctatggtcc cagctactaa 16380
ggaagctgaa ggaggaggat tgcttgagcc tgggaggtca aggctgcagt cacccacccct 16440 gggtgacaga gcaagaccct gttacacaca caaaaatgat aaatcccaag aatcagtgac 16500
tgacataggc attcacataa tatcttcaga attgaaaggc aaccagtttt tactgccctt 16560
acttccagcc tattctattt ttgtcagttt taggacaacc taccttatta gctgttggtt 16620
```

```
attgatcacc tgcggagatg atggttgtct gctatgtaac ctgccaccat ggcagtaaag  16680
aagggagtgg gggaagggtg ataatcctta tattctgcag ttttctcact ttaatcaggt  16740
aggttaaata acatatccaa catcagatgt aggttgtagt ggttctagtg tacttattct  16800
ttctgcaacc ttatgatgtc ttttaaatcc aagatccttt cagtaacgga gtactgaact  16860
gtttttgtag ctctatcaag gcttgtcaag cagtgtgctc atcacatggt aaatcatgca  16920
gcgtggaacc tcataaaatc tccaagaaac atcattcacc catactgact agtttcacat  16980
ctctttggta agtgatagta ggaaaccttt ttcccctggt ttaaaaagga tggatgcaat  17040
aacatttata ggtaagactg aggagcattt taaaaaccac aggccgggca cagtggctca  17100
tgcctgtaac cctagcactt tgggaggctg aaacagttgg atcacctgag gtcaggagtt  17160
tgagaccagc ctggcagtg tggtgaaaca cggggcatcc accaagagaa ataaatcaaa  17220
gtccaagtac ttgaattcat aatctgagga gagaggtgta tgtaaacaaa acacattcag  17280
tgtgacaatg tcagagagta tatggggttg ctttggccct gtagaagagg tacttggcct  17340
gttttggaga aagatgggaa tgcttcatag tgtgcttcat agtggatgta aagtttgctg  17400
attcttgaag ggtgagtagg atttccccta gcaagcacta ttggaaggca taatcaatgt  17460
ataaaagcac agagacctgg agaggagtgg gaagcaagtt cagtcagttt aaacaaatgt  17520
tttgaaaatg ttaatctgtg cagttcaaag acattagaat agaacaggtt gaaacaatac  17580
tgattgaatt tattggttat gggactattt atggttttca ttttttgtgt cagttttgt  17640 tttttctccc tgagaatcag actgggatct tgtatcagtt ttgataaatt attttcttc  17700 tgggaatttc aagtttgtgg gcacaaagtt gttcgtgata ttgtcttatc ttttaccat  17760 ctgtaggatc tgtagtgatg tatcatttcc attcttgata ctggacattt accctaattc  17820
atccctcact ccctcatttc cattcttgat attggacatt taccctaata ttcattctct  17880
ctctctctct ctctctctct ctctctctct ctctctctgt ctgtctctct ctctttctct  17940
ctctctctct cattctttct ttcttttttt gagacagagt ctcactgtcg ccaggctgga  18000
gtgcagtggc atgatctcag ctcactgcaa cctctgccgc ctcccgggtt caagcgattc  18060
tcctgcctta tcctcctgct gggactacag gcgtgtggca ccacacccag ctaatttttt  18120
atatttttag tagagatggg gtttcaccat attggccaga ctggtctcga gctcctgacc  18180
ttgtgatccg cctgcttcag cctcccaaag tgctgggatt acaggtatga gccatcacac  18240
ctggcccttc tttttttttt tcttaaatca agcacactta cattttaat ttcttccccc  18300 ccacctgcag aggcagggtc tttctctgtc gccctggcta gagtgcagtg acatgatcat  18360
agctcactgc agcctcaaac tcctgggctc aagtgatctt cctgccttag cctcctgagt  18420
agctgggact cagctaattt tttccattgt ttttattatt aaaaacaatt tttttgagat  18480
ggagtctcac tgtattgccc aggctggtct caaactcctg gctcaagca gtcttcccgc  18540 ttcagccttc ctaagtattg ggattacagt catgagccac catgcctggc ctaatttta  18600 aattattttt gtagagattg ggggttgcac tctgttgccc aggctgatct caaactcctg  18660
gactcagaca atcctttgcc ttggcctttc aaagtgttgg gattacaggc atgagccacg  18720
ggctcagcac gagcatttt aaagactcaa ttggtattgt ggatcctctt tgtttcatat  18780
ttctttgatt gctgcttttc ccgtttttt ccttctagtt tctctgggct tctgttttca  18840
aatttattga gatatgtgta agttcttaat ttttagtttg cttttctaag ttcaagttta  18900
tgaattttta ttttcgaatc agggccttgc tatgtcgccc aggctagagt gcagtggcat  18960
```

```
aatcacagct cactgcagcc tccacctcct aggctcaagt gttcctccca tctcagactc  19020
ctgaatagtt ggaccacagg tgcatgccac cacacctggc tttttttttt tttttttttt  19080
tttaatagtt ttaagttaaa aaaatagaga cagggtctca ctatgttgcc taggctggtc  19140
tccaaactcc tgagctcaag caatcctcac accttggcct cagcctccca aagtgttggg  19200
attacaggca ttagccactg tgcacagcct aattattatt attttttttt tcttttttt  19260 tttttttttg agatggagtc tcgctctgtc gcccaggctg gagtgcagtg gcacgatctc  19320
ggctcactgc aagctctgcc tcccgggttc acgccattct cttgcctcag cctcctgagt  19380
agctgggatt acaggcgccc gccaccatgc ccagctaatt tttgtatttt tagtagagac  19440
ggggtttcac catgttagcc agggtggtct cgatcttctg acctcgtgat ccgcccgcct  19500
cagcctccca cagtgctggg attacaggcg tgagccactg cgcccagccg attttaaaa  19560 tttttatttt tatagaggcg aggtctcgcc atgttgccca ggctggtctc gaactcctag  19620
attcaagtaa tccactcacc tcagcctccc aaagtgctgg gattacaggc atgagcaacc  19680
acacctggcc taagtttata aatttctaag tcctgcttta attgtatccc acgttttgaa  19740
atatcgtatt tttatgaaca aactctctat agcctatgtt ttttttatt taaaatttat  19800 tgattgattg attttgaggc agagtgtctg tcagccaggt tggagtgcaa cactgtgatc  19860
atagctcact gaagcctcaa actcctaggt tcacatgatc acttcagcct tctgagtagc  19920
taggacacag gtgcatgcac catacttagc taacttttaa atttttctgt agagatggta  19980
gtcttgctgt gttgcccagg ctggtcacga actcagcctc aagccatctt tcctcttcag  20040
tctcccaaag tgcagggacc cctgagctgt gcccagctct taatttctaa ttgatacata  20100
attgtacata tttatgggat atattgtgat gtttcagtgc atgtatacat cgtgtatata  20160
atatataccc catgttttag atgtatctct tttttttttt tttttttttt tgagatggag  20220
tctccgtcac ccatgctgga gtgcccactg caacctccac ctcctaggtt caagcgattc  20280
tccagcctca gcctcctgag tagctgggat tataggcacc cgccaccaca cccagctaat  20340
ttttgtgttt tgttgttgtt gttgttttta agtagagatg aggtttcgct gtgttggcca  20400
ggctggtctc aaactcctga cctcaagtga gccaccacac ctggcctaga tgtatctctt  20460
ttatttattt gtttattaat tttttttttt ttttttttga gaaggagcct ccctctgtct  20520
cccaggctgg aatgcaatgg cgttatcttg ctacaacctt cgcctctcga gagtttcaag  20580
cgattcccct gcctcagcct ctaagagcag ctgggactac aggcacgcac caccacaccc  20640
agctcatttt tgtattttta gtagagatgg gtttcactgt actggccagg tggttttga  20700 gctcctgacc tcaggtgatc tgcccacctc agcctcccaa agtgctggga ttacaggcgt  20760
gagcagctgc acccggccta gatgtatctc ttttagacag catgtgatag aattttttc  20820 cttttttaa attttttttt aaattaatac acagtaaaat tgactccttt ttgtgtatac  20880
tgttctatga attttaatac atacatagat tcaagtaact accatcacaa ctgggacata  20940
gaatagttat atcaccttct gcatgttacc cttggtaaca tacctagcct cccacccta  21000 atctctagca accactgttc tgttctgagt tactacagtt tttttttttt tttttttttt  21060
tgagatggag tcttgctctg tcgcccaggc tggagtgcat tggcgtgatc tcagctcact  21120
gcaagctcag cctcccgagt agttgggact acaggcgccc accaccgctc ccggctaatt  21180
ttttatattt ttagtagaga cggggtttca ccgtgttagc caggatggtc tcgatctcct  21240
gaccttgtga tccatccgct tcggcctccc aaagtgctgg gattacaggc gtgagccacc  21300
gtgcccaacc tcactacagt tttatctttt cgtgaatgtc atataaatga aatcaaacat  21360
```

-continued

```
tatgtaatat tttgagactg gcttatttca ttcagcatac tgcctctgag attcatcaaa    21420
gttattgtgt gtgtaaatgg ttagttcctt tttattactg agtagtattc catttatgga    21480
tagactatag ttatttttat ccattcactc cttgaaggac attttggttt tcattctttg    21540
gtgattatga atacagttgc tgtgaacata acattatagg cttttgtgga cctaagtttt    21600
cattttccta gggtaaataa ctgtgagttg gattgctggg tcatatgaaa aatgtacatt    21660
taacttattt ataagaagt tgccaaactg ttttctagaa tggctataca gtactatttt    21720
gcgttcacac tagcaatgta tgagtttcag tttttcctca tcttctctag catctcatcc    21780
tctttagcat ttcaagttaa atattggcag tatttaactt gtaatgttga aaattttagg    21840
tttacagaag ttacagatag aatctccata tatgcttccc tcagtatatc ctaatgttca    21900
catcttgcca taaccgtgat atgtcatcaa cactaagaaa ctgggccagt catggtggct    21960
cacacctgtt atcccagtaa ctctggaggc cgtggtgggg aggattgctt gaggccaggc    22020
gtttgagacc aacctggttc tcagaagtta ggtgggcatg gtggcatgtg cctgtagtcc    22080
tagctactta ggaggctggg gcaggaggat cgcttgagcc caggagtttg aggctgctgt    22140
gaactgggag agctaggatc acaccattgc actccagcct gggtgacaaa gtgagacccc    22200
atctctaaaa ataaataaat aaataaaata attaagaaat taacatcggt ataatactat    22260
taactaaact acaggctttg tttggatttt accagttgta tccttttct gttcaaggag    22320 ccagtccagg ataccacatt aatttagtca tcatgtctcc ttagtatcct ccagtctgtg    22380
aagcttctta gtctgtcttt aattttcatt acttggaaac ttttgaagaa gactggtgat    22440
gtatgttata gaatgtcctt caatacaggt ttgatgtttt ctcaagatta aattgtggtt    22500 atggatttt gagaagacta ccacagaggt gaagtgccct tctcatcaca ttatatcagg    22560
ggcatatgat gtcaaagtga cttaacacta gtgatatttc agtaaagtct gccaggtttt    22620
tctactgtag agttgctatt tctcccttc caagcccatt ggacttagga ataccttgt    22680 aatgaataag catggaaagg gagaaattta ggctctcttt ccatgcttac ttatttcctt    22740
tccttaaagg agaaaaattg agctccacct cctagattcc tcacatgtgc agttcacaat    22800
agggttctcc tatgagaatc taatgctgtt gctgatggga caggaggcag agctcgggca    22860
gtaatgcgag tgactcccgc tgctcacctc ctgctgtgta gcctggttcc taacaggcca    22920
tgaactggta caggcccatg gcccggggat tggggacccc tgatataaat ggaagtatac    22980
aatatgtagg cttttgtttc tggcttcttc acttttaaga ttcaccatgt tggtcaggtg    23040
tagcagctca cacctgtaat cctagcactt tgggagactg aagccaaagg attacttgag    23100
gctagacgtt tgagaccagc ctgggcaaca aagcgagacc ctgtctctac caaaaaaga    23160 aaaacgattc atccattttg ttgcacaaat cagtaatttg ttccttttta ttgctaagca    23220
tcacatggca aaccatttgt ttgttcatgt aactgttgga caccttggtt gtttctgttt    23280
tttcacaatt atgaataaag ctgccttaaa tgtttgtgta taagttttg tgtagatacg    23340 ggtttccgtt tctcttgagt aaatacctag gagtgggaat gctggttgta tgcttaagta    23400
catgtttaac tctataagaa actgccaaac tgttttccaa aaccattttg cattcctacc    23460
aggaatgtat tagttactgt tactctgcat ccacaccagc ttttggtata gttttgtttt    23520 ctgtttttt aaattttagc cattttaata aatctgtagt ggtagttgta tgatttaatt    23580
tcattttccc tgctgtctgg cagtgttgtg tatcttttca tatacttatg tgtatatctt    23640
cttttgtggt gtgtatgttc acgtcttttg cccatttta aattgagctg ttttcttatt    23700
```

```
gagtttttta atgttacaga tacaagttct ttattcgatt tgtgatttgc aaatacattc    23760
ttcttgtgtc tggcttattt tcttaatagt gtctttcaca gagcagaaat attttaacgt    23820
tgatgaagtt cagtttatca gttttacagc ccatgctttt agtgtcatgt cttcaaactc    23880
tgcctaaccc ctggttgcaa gaaggtttga aattttaca tttatatctt ttttttttccc    23940 ccccagaggt agagtcttgc cttgtcaccc agcctgggat tatacagtca tgagccaccg    24000
catctgaccc aagttttaca ttgatatctg tgattcatta tgaattatct ttatataaag    24060
tgtgagattt agattaaagt ttatgatttt gcatattgat ctccaagtct tccaaaacaa    24120
tttatagaaa agattattat gcctgtaatc ccagcacttt gggaggccaa ggcaggtgga    24180
tcagttgagc tcagaaattt gagaccagcc taggcaatat ggtgaaaccc tgtctctact    24240
aaaaatacaa aaattagcag ggcatagtga cacactcctg tggtcctagc tactttggag    24300
gctgaggcag gagaatcact tgaacccagg aggcggaggt tgcagtgagt tgagatcatg    24360
cccctgcact ccagcgtggg caccagaggc agaccctatc tcgaaaaaaa tacataatat    24420
atttatatat atatgtatat atgtcctttc tccattgaac tgcctttgta cctttgtcaa    24480
aaattaattg gccttgtttg tgtgagtgta tttctgtact ctttattctg ttcccttgat    24540
ctatgtatta tcctttttgcc aatacactgt tttgacaact atagctttgt aataagttta    24600
agatcagtta gtataattct tccagcttta ttattttttca gaattgtttg gattattctg    24660
gttcatttgg atttcttttt taatccagtc tgatatgata gtctttgtct tttacctgga    24720
taatttattc cacttatatt taatataatt aatcatattc caattcaact ttcttcccct    24780
atgcttctta tgttctagat ttttttcttc tcccttctta acattctttt ggattctttt    24840
tatgatttta cttttccctc tttctggttt ggaaatatat gctattttta ttctgtaatt    24900
agttgtcata catcttgtga cttgcagcta taacttagca aaacctgata ttataatttt    24960
atcttctttt catataataa aagaccttta gaaagaatac tttgaaatct cctcaataca    25020
ctgtgttttt attgttatgt attctatgtt ttaaagctcc tcaaggtatt gttattctttt    25080 tgtataatca gtgtttgttt ggagctgtct gtaaattttc ctcttttttg ctctttattt    25140
tttctttcaa ctcagacctt ccaaaatggg attattttttc tttttttctttt agagacattt    25200 gcttgataac agaattttaa tttggcggct atttattttt ttcagcacac tgcaggtatt    25260
aaactacttg gcttcattgt tggttttgaa aaatcagctg ttctaatgtt gctctttgaa    25320
tataatctgc ctttttctgt acttgcttgt ctttagtttt ttgttttttgt ttgagacaag    25380 gtcttgctgt tttgcccagg ctggcctcca actcctgggc acaagcaatc ttcctgtatc    25440
agcctcccaa atagctggga ctataggcct gtgccattac acccaactca tcttttgttttt    25500 ttcctgctat tttgtaatta tatgtttggt tttggatttc tttttattga tcttgtttgg    25560
aaattgtttg cttctggaat ttgattgtgt ctgattgctt ctgggatatt ttcaactgtc    25620
ttcagttact gcctttatcc cattctcttt tctgctagta ccaattaaaa gtatatcaaa    25680
ctggctgggc acggtggctt acgcctataa tcacagcact ttgggaggcc aagatgggcg    25740
ggtcacttga ggtcagaagt tcaagaccag cctggccaaa acatggcaaa accccctcac    25800
tactaaaaat acaaaaatta gccgggcatg gtggcatgca cctgtagtcc cagctactct    25860
ggaggctgag gcaggagaat cacttgaacc tgggaggcag aggttgcaat gaactgagat    25920
cgtgccactg cactctaacc tgggtggcag aacaagactt tgtggcaaaa aaaaaaaaaa    25980 aaaaagtat atccaacgat ttcactatat ttttcctctt gttttttgag atctgctagg    26040
acattgtatt taaaaataaa taattggctg ggtgcggtgg ctcacacctg taatcccagc    26100
```

-continued

```
actttgggag gccaaggcgg gtggatcacg aggtcaggag atcgagaccg tcctggctaa 26160
cacggtgaaa ccccgtcttt acttaaaaaa aaaaaaaaaa aaaaaattag ccgggcgtgg 26220
tggcggactc ctgtagtccc agctactcgg gaggctgagg caggagaatg gcgtgaaccc 26280
aggaagcaga gcttgcagtg agctgagatc aggccactgt actccagcct gggtgacaga 26340
gcgagactct gtctcaaaaa aataaaaaat aataaaata aaaatagata tttgtagtga 26400
tcatttgagg cccacagtaa ggtactttcc tccatggaga gcttgcttat atcaggtatg 26460
catgggcact aatccagaga ccaccttaaa acaagcttaa gatatgatat tcccttcagt 26520
agggctttaa ttcctccctg gatcttccac tccctagtca ctctcaccat taggaagtat 26580
gcctctgaag tcccaccttg tgaagagggc ctcctattag acttttttgtc ttgtgagagc 26640 cctgggcttt ggtttatgtg agaacaaaat tctaattttc aggatcaaca aaggctttcc 26700
aggcttcctt gcttgcttat atctctgggt ttgcattttc tattcccttt tggctataat 26760
tacttctctg tcttatttaa agatgagtgg gccaggtgtg gtgacacatg cctgtagcct 26820
cagttacttg ggaggctgag gtgggaggat tacttgagcc caggaatttg aagtggcagt 26880
gagctacgat tgtgccactg cactccagct tgggcaacaa ggaactgatt agtgttggaa 26940
gtagagaaaa gaaataaag agaaagaatt ccaaagcttg tgaattaatg atactgtttg 27000
ttttaagcac aaaatggtaa cagtcgagta aactaatagt ctccaaatca gatataaaaa 27060
ggttgctgac ctgatgtgca aaaaagcac atcaggtgct tttttacacc tgatgccacg 27120
ttgcatgtgg catccaatga tgtgtttctt atagaagata acaaaatgtg ccagcctttg 27180
gtcattttag ggtgcaaaat tataggtctt taaaattctt aacttgcttt aaagtgttac 27240
gctttgcaat ttcttgtttt aatgtttttcc atctgaataa ttcctgtgcg tactttaagt 27300 gcagttttt ttttctctta cagttttttcc ccatttttagg tactccataa atatttgttg 27360
aatgaatgat gggttggtga tagtttaaat acccttcaac gtctgtacac caccatgact 27420
taattgtttc aagcactgat cacttgagat tgtaatggtc tgttttcttt gtctgagggc 27480
agagatactt tctccaggac caagagaaag aatgcctttc tggcagtcag gcacacattt 27540
cctggtacat agtaaacgtt cagtaaatgc ttgatgtatg agcattctgc tcttgattgg 27600
aaaggaagaa agaaattaag gttaagtatg gacatttgaa ataagtaatt caggtaacat 27660
tagctacttg tgcttttttg tattaagttg gccttctaat cagtgcccct tttgtaaagg 27720
gaaatgggca agtttgactg aatttttctc tttgcttctg tagcaaggta gaaaagtata 27780
catatttaag gtctcgctga gttccacaag tcttgtttgt ctcttaccag tttatgttgc 27840
ctgattgctt ggaaaaagag ttcattctct gcagcagtgc ataaaggtg tcttcctgta 27900 tagctgcttt tcctctaaac aagcagtcct aaaccatgca gtcagtgcaa tctaagcaca 27960
ttcctcattc tttgctatag aaatctttgt cctgtcggga tgatgatgag atcttgttca 28020
tttgctatgg ttcatttagg gatgagaagg agatttttt tttcctttta agatggagac 28080
taataaacat tagggttaaa aagaactaat tatattacag ttcaaaaatt gacttaaagt 28140
tctagaatga tcttttccat ttctgatact aggaaattca tcaataaaaa tacattagca 28200
gaaatgacta agcaaacttg tttgtatagt tttctggtat tggactgtta ctaagcctct 28260 agttttctt ttagttgcca aattgaaaaa taacaactga acataagaga ttagaaggag 28320
ggactagcta agggcaagag gagttttat tgaaattaat tctgctgtat tcagtgtata 28380
tcagtaaact tatgattttg gcaatggaca attttttcctt atggtttaat ggcattttct 28440
```

```
ttttatttac ttatactttta ttaaagaata ggtcatgcag acccatgcag ttggcttcga   28500
tgtgatctta cttcagtcgg gaaaaattca ttgacatgat acttttttcg tagctgatta   28560
attggcttct gttaggctaa acgttgagca tacaagacct agccatgtct tcaaagtcat   28620
tctgacggtg ttaaggtaga tgtagtggtc tgaaatggtt agccactaaa gttacacctc   28680
cttttatgca attacatgag aacagtaagc actaagtaag acaatttaaa atggaactta   28740
ataagaaagg cagtgcattt tgttagattg ccttaagata tactagtatt atgaacagtg   28800
gagaggagaa ttgatcttcc aaatatctag gactcaggca cttttccat cttccaaata    28860 agctgctata aaaattggta aaatcaagtt tcttcagtat tctcttaatt tgaattatcg   28920
aggggaaaaa gacaaatcct agttgtagtc ctgtgattta atagaagctg tagtattggg   28980
aaagagagag agggaaggga acaattactc aagaaccttt gacttggttt tccagttctc   29040
ctagttgcgt accagatgac ctgaagtatt taggaacacc ctatactttg gatgcaactt   29100
cattttcatt tcattttta aaaataaacc aagattaatt tgatcaccaa atagtgttta    29160
ctgaacgtgc tacaaaatgc aagccttagg ctaggtacta taaattaaaa aggtaaatta   29220
aacatggttc ttaactttgt agaacttagg gtccaattga gaaattaaga tttgaagact   29280
ggtgtgtgtg tgtgtgaatg tgcagtagaa agtgattgtg ttctgtagga gtgagaagac   29340
ttgaaccttg gaggccaact cactgtcttt gaatcccagc tgtaactgta ttggatattc   29400
ttggtcaagc tactgaactt aggctgttct tatttgtaga ttagagaaac taatgcttgc   29460
ctcgtagagt tgttggaaga gttagatact taaagctgag aaactcttag ttccagactt   29520
gtaatatcta actgcctatt cagaatcttc gtttgaatga ttcaaagcca ttttaacctt   29580
aagtccaaaa cctatcttgt gcactcttat ctccatgaat ggcaccaaca gtctgtcaag   29640
caagaaatcc aagagtcacc tcccacttca tacagcattt tccagttcac tcagagctat   29700
tgattttaca ccataaattt tgttcctcat attagtccac tgatctccac atgccaccac   29760
cttaggtcat catttctctc acgtgtgcta ctgttaacag ccttctccct aagtcctgtc   29820
ccacactcag ccagagtaaa aattttaaaa acaatatgta tgggtcactt ttctgcttaa   29880
aacttttcaa tgaatttctg ttacccttag tccataggta aaatcttcaa tggcatactt   29940
gtctcacccc tgttctgcct tgctcactta tattcctaag gcctaggata gtactttttc   30000
atagtagatg gttatctatt taagggatgg acaaaatcag gaatgtaggg aagaatcaaa   30060
ccaaaaattg agaaatgtag gctgtgtgtt ttcttcctgt tagcttacat gtgatataca   30120
tatgcatttg cagaggtata agtgaaatac tatttctaaa taagataatg tttatcttgg   30180
ttgggcatgg tggctcacac ctgtaatctc agcacttcgg gaggctgagg ctggtggatc   30240
acttgagtcc aggagtttga gaccagcctg gcatcatga caaaaccttg tctctacaaa    30300
aaatacaaat attagctggg cctgatggcg catagctata gtcccaacta ctcaggaggc   30360
tgaggtggga ggattgctca agcccaggag atgaggtgga ggtttcagtg agccgagcga   30420
gattgcacca ctgcactcca gcctgggtga cagcgcaaga ccctgtctcc tgtctcaaaa   30480
aaataataat gataatattt ggtctttgac ctcccttttc tgtcttttca catcccctct   30540 tgttttttgtt ttttgtttgt ttgtttgttt gtttttgaga cagggtcttg ctctgtcacc   30600
caggttggag tgcagtggtg agatcatggc tcactgcaac cttgacctcc caggctcaag   30660
tgatccttcc atctcagcct accaagtacc tgggaccaca gttgtactcc actacaccca   30720
gctcattttt atgttatttg tagagaggag gtctcgctgt gttgcccagg gtggtctcaa   30780
actcctgggc tcaagtgatc ctgccagagt gctgggatta taggtatgag ccaccacact   30840
```

-continued

```
gggcttcaca tcccctttttt atcaccatcc cttaacccccc aatctcttag tacccttttta  30900 tctatctgag attacagagt cacagttgaa gaatcctctg ttttattttc ccgtataatt  30960
aatgaaggcc agccatttga aattcatgtg aatacctttc ttactataag cagattattt  31020
ggtatgcgtg acagtaaggt gaagcacctc tttgggggta ctgcaaaaat agttagcttg  31080
ttgtcttccc agtggagaat cagatctgct agttcataaa ttaggtccca gttgatgagc  31140
cccaaagctt caagggtcat tcagacaagt actggagaat ctcaagagtt cattagtta  31200 ttagtctttt cccactcctc acagaggatg ccagggcctt gaaacagcag aagaagactg  31260
ggtgatgaga atgtacatga ctagtaatag gagttggcta ttctccatat gtcagatggt  31320
ttccagggag aaatgaggac tcattttgta atgtcatgta tacttgggag ttagccctca  31380
gtggccggga attaaccacg gctactataa ttttttgtatt ttaaagaatg aaggttccag  31440
cctgtaaaga taggtttctg cttattagct ttcactaagg agctagggga tagtaattac  31500
ttaatacaaa tttacatgca tttcatgttt ctaagccctt tctggaagat catctcactt  31560
catcttccct tcagtctgca agcacagtta gacaggtttt ataagtgatg aaccaaagct  31620
gggaaaagcc caacagagag atcactttta agcataggaa aagggctttg agatccacag  31680
acgaaggctg tcttacacgt ataaaatgtt aaccagaaga gtaaagtggc tgtaaaggtt  31740
atgtagagaa agatactgtt tcctgtcaga ggagaggctg agaatttaaa agtttagtat  31800
attaaaagta ataaatttct ggggacagca tttctgttgg gttcatgctg ctgtttctac  31860
tattttggcc atattcacac ctacacctt ctctacggtt ttcctagtgt cttcattgc  31920 tgtcaaggca ggcatagtag tcacagagtc accaatccta caacatagat gaccttattt  31980 cttttgggaag aagaaaaatt acaagaaaac atctggtttt tgcatgtttg atgtgtttgt  32040
gtgtgtgtgc gtttacagtt ttaactgata ttaagtgaag atagattaat gtcacccagg  32100
ttttacaaaa tcaaagaaat agaaataatt ttaaagactt ttggtacttg aattactttg  32160
ttgttttctg gtcattagt acatttatgg aacctcagaa ggtttgagtt gaacagaggc  32220
aagttacagc agttttttgg gtgggagaat tcataagtca gcatgtgaat cttttgatct  32280
catatatttg gagtggaatg tcattaattg tgtttgtcac ggttaaggaa tagagaatta  32340
atctccatcc cagtcttgct attcttctga aagcctttag ctgccgacac catgggcata  32400
aggaggtatc tcttctggct tctctttggg tgtggtagct aagttacagc ttaccttgga  32460
aagatgagca gcttgtaagc aacaaaaaaa cagtatagtt aacaaatgca tcgtcaacaa  32520
acaaaacaac ccaatcaaaa aatggacaac agctttgaat agacattctc caaacaaat  32580 atacaaatgg ccaataagca tgtaaaaaga tgctcaacat cattaatcat tagggaaatg  32640
caaattaaaa tcacagtcaa tgagatacaa cttcatactc attaggaggg ctgttactga  32700
aaaaaaaaaa agaagaagaa gaaaagaaaa ccaaaaaata ggccaggcac agtctatttt  32760
gagagcactt tgggaggccg aggtgggagg atcccttgag gccaggagct caagaccagc  32820
ctgggcataa gcaagaccc tgtctctata aaaacaagca aaaacagaa aataacaagt  32880 gttagtaagg atgtagagaa gttgtagcct ttgcactgtt cctgggagtg taaatgata  32940 cagttgctgt ataggagtga gccaccgtgc ccagcttgtt gaaacaatat gctggttctt  33000
caaaaaatta acatagaatt actacatggt tcagcagttc cacttctgga tatatacata  33060
aaagatttga aagcgaggtc tcaaacagat gtttgtacac ctatgttcat agcagcatta  33120
tttacaatag ccaagctgtg gaagcaactc aagtgtccat cagcagataa atggataagc  33180
```

-continued

```
aaaatgtggt gtgtgtgtgt gtgtgtgtgt gtgtgtatat atatacacag tgcaatatca  33240
ttcagccttt aaaaggattg gaattctaac acatgctaca acatggatca gccttgaaga  33300
cattatgcta aattaaataa acaaaacaaa ggacaaatat tgtctgattc cacttatatg  33360
aggttcctag aatagccagc tcaggcagaa aatagaatag tggttgcaaa gagttggggg  33420
agggaaaatt agtgtttagt ggatacatag ttttcatttg ggatggtaaa aatttgtaga  33480
aatggatgat ctggtgatta ctgcacaaga atgtgaatat acttaatgca actgagcttt  33540
aggtttaaat gtggataaaa tggcagtttt tattttttt agatgaggtc tctctcctgt  33600
cacccaggct ggagtgcagt ggtgcaatca cagctcactg tagcctcgac ttcctggtct  33660
ctggtgattc tcctgcctca gcctcccaag tagctgggac tgcaggcaga caccatcaca  33720
cctggctaat ttttttgtatt ttcagtagag atggggtttt accatgttgc ccagactggt  33780
tgcgaactcc tgggttcaag cgatccaccc tcttaagcct cccaaagtga gccactgtgc  33840
ctggccataa agtttatgtt atgtatattt taccacaatt taaaaagtg tttcaacaag  33900 ctgggtatgg tggatcactc ctataatcac agtactttgg gaggctgtgg tgggagcatc  33960
acttgaaccc aggagtttga gaccagcctg ggcaacatag ggaaacccca tctttacaaa  34020
aaaaaaattt atttaattag ccagctgtgg tagcccacgc ctgtggtccc aactacttgg  34080
gaggcagagg tgggaggatt gattgagcct gggaggtcaa ggctgcagtg agctgtgatc  34140
agaccactgt actctagcct ggcctacaga gggagacctt gtttcaaata agaagatttc  34200
aacaaaaagt aaataaaaat agtacaaagg gcatctctat tcccttacg cacgtttacc  34260 tattgtaata ttttacccag cttgtttat catttgtgag tgtgcagtca tgtgtgctat  34320
atatatacac atgtaaacgt gtgggcacat tttttcctg aatcatttta gggtagatta  34380
tatgcatcat ggctgtttac ttctaattac ttcaggaaaa tttcttaaca atagacatat  34440
tcttgggctg gcgaggtgg ctcacgcctg taatcctagc actttgggag gccgaggagg  34500
gcggatcacc tgaggtcggg agtttgagac cagcctgacc aacatagaga aaccctatct  34560
ctactaaaaa tacaaaatta gccaggcatg gtggcgcatg cctgtaatcc cagctactcg  34620
ggaggctgag gcaggagaat cacatgaacc tgggaggcgg cagaggttgt ggtgagccaa  34680
gatcacgcca ttgcactcca gcctgagcaa caagagcgaa actccatctc aaaaaaaaaa  34740 aaaaagaat aggtatattc tcttaactat tgtgattatg taccaacttc acaaatttac  34800
attgatacaa taatttaata ccctctgaat tccagttctg tcgatattgt tttttatagc  34860
atccccctcc acctcctgca gtatgggata cagtctagag tattgcattt atgcaatgtc  34920
tctttagcct ccatttgtct tttatgctgt ggacatgttt tagaagtata gtaccccttc  34980
ccccttttta aatagacact tcctcttttt ctgaatgttt cctggtaatt gaattgaagt  35040
tatggctggg tgcggtggct cacatctgtg atctcagcac tttgggaggc tgaggtggga  35100
ggattgcttg agcctgggag ttcaagacca gcctgggcaa catggtgaaa caccgtctct  35160
actgaaaata cagaaaatta gctgagggtg tggtgcgtg cctgtagtct cagctacctg  35220
ggaggctgag gtgaaagaat caccggagtc caggaagttg aggcttcagt gagccatgat  35280
cacaccactg cattccagtc tgggcagtgg aataagaccc tgtcttaaaa cacatacaca  35340
catacaaatt gaagttatgc tgtctcagcc aggagacttg catacgtgtt atatccttct  35400
cacgttatca caatctggag actcaataca atttcatcta aatgcataat gagggaatc  35460 agcacatgct gtaggagata gggaagacat cattggaaag gaacctgatt tgatagcata  35520
tttctaacat cttacttatt ttccccggt gtcaaatttt gcattagctc agctaatctg  35580
```

```
tattactgtt ttataccagt ttttaagctc ctgtattaaa tataaagaga atattactga   35640
tttctgtttt taaatttaat gaaaccaagt gtgtctttca aatggtgatc aaggttctac   35700
tgattattac cttaaggttc ccccaaaaga tttggattgg tataagatga catggagctt   35760
tgatgtatga gaacaagcct ttattctctt cctggtttca tcaaatatga gtcagaatgg   35820
caagttgtac tcttagcttt gccgccattc tagaaccttt tagcacccct acttaagtta   35880
cagaaagctg ctgaaaagaa agtatttttc ttgccaatac cttttgtaga atatataact   35940
agtggtaatg ctgatgtatc tatcctcaat gccattttc tcttccaggc tgtcttacaa    36000
aaatcattca aattttgcct gcagaggtaa caggatattt ggcaaaatat gattaaagca   36060
aatatcagtt tactgtattt cttgggatttt ttcttctcat gttataggaa gcactggtta   36120
acacagttga gctatattta ttggctgtag gtaggagagc cagaggtata tttcaggcca   36180
ttattatttg taagattatt tccttcccat ataccttctg taaatgattc cttggacttt   36240
gtgcattttg tttctgcagt ttgaagaaaa caggtctgaa acaaggtctt accccccagct  36300 gcttctgaac acagtgactg ccagatctcc aaacatcaag tccagctttg tccgccaacc   36360
tgtctgacat gtcgggaccc gtgccaagca gggccagagt ttacacagat gttaatacac   36420
acagacctcg agaatactgg gattacgagt cacatgtggg ggaatggggg taattgtttt    36480
tgttgacttc attatactca ctcaaagggc tgaatcttgt ggatctgttg agtagttttt   36540
gtcagaaaac ctccgtgact ctgtatgtgt atacctcagg atcaaagccc aatttgtgtt   36600
ttcttttgag ctgaaaattt ggttttgcag tgaggaagca gagttgcttt ggcaagtgaa   36660
caattttaat gggcttacca ttttaaaaatc attttagttt cttatccttt tctatgtgt    36720 atatgcagtc gtgcaccaca taacaaagtt tgaattaatg acagaccaca tgtaggacag   36780
tggttccata agattataag agagctgaaa aatgtctgtg gcctagtgat gtcatcgtaa   36840
catcaacagt gcattcatta ccttttctac gtttagatac acaaatacca ttgtgttaca   36900
attgcctaaa gtatttatta cggtacacat ttgtatccta ggagccgtag gccatacccct  36960 aggtatgtaa tatgccatac catgtaggtt tgtgtaaaca ctctgatgtt taacacattt   37020
ctcagaatgt cattaaataa cgcatgacgg tattctgtat gggcacctgg caacaaaaag   37080
ttacctatca gcttgcttat caagccaagg gcattgcaga tcagtgagaa gtgatacttg   37140
agagactttg aaaacaccaa agtcttatat aaagtatttt tgaggtagag aatgttgttt   37200
cgtgttaata caggaggacg aaacagttct ccaaagaggt aacttctttc tgatgagaaa   37260
caattaaatt cttaaacatt tgcccttatc ctgagactag gcatgtctta gcatggaatt   37320
cagcccaaat tctatcttga acagttgtag tctgcctgaa cagctgtgtt tgccctccta   37380
attctctgtg cagactcatt tggatgtttg catttcctgt cccaatgtgg tagacattta   37440
attgttcaga tcatactttt gtgataaaag cattttgaca ttcaagtgca aagaaagca    37500 atttgaaaac taaagctaca gctcctgtat gctgtatttt atatctgact gcatgtgatt   37560
tctgtaacct gtaagtggtt agtggatggc ttccctaaat tgtcataggg cgtatttta    37620 atcttgagta tgccatgaat ttgtgtatgt gtgtgtgtgg aaatgagtct tgctctgttg   37680
ccctggctgc agtgcagtgg tgtgatctcg gctcactgca gcctccgcct cctgggttca   37740
cgtgattctc ccacctcagc ctctcgagta gctgggatta caggcacctt ccaccctacc   37800
cagctaattt gagtatgcca tgattcttaa cagtaaaatac attgcctctg aatacagagg   37860
cactgtatgc tgtaaagaca ccattaaatg ccagtgtggt ttagtaccaa taaatgttgt   37920
```

```
tattactgat aatctaacaa ttctcctctt atgtcacagg cttggactc taggtgacac 37980
tgtgtttact ataggaattt cagccgctat cttcaaattg agtgctttgc acttggttct 38040
gcttaaatgg cactaaagag ccctttgggg cttttggcat ggttctgttt gcttgctggc 38100
atttgttttg tatgccctcc cataggaaga gaactcaacc agaagtagga gcattcttcc 38160
cctacacctg ccatgattat tatgttgtcc attgttttta gtacctttg tcttttcatt 38220
cactttcttt ttagctactt gaggaaaatg aatggttgag gtggttgatt tggttcatat 38280
tggatactta gtaggtccag aggattctat ccagtaggat agaatttagg ccttattgga 38340
actgtgtttg tcattcttca gagcaaagcg ctctacattg gaagcaggca gggcaggag 38400
gaaaatgttg gcatttccct tattctacct ctgtttatta cctctgatgt tgcttattgg 38460
tcacagaata tgggtatatg tagaggaggg gatcgctgat tatagtttac aatctataat 38520
gtgcttcgta ctacgcatgg actatccccca gagcttgccc tggagggcaa atagattaag 38580
cctatacatt tgaaagccat ttaccttcaa agaggcctgt taaaaatcag ctgctgccaa 38640
agtgtggcta gattgaaaca gtcttgcaaa atgtttttag ttcctgctaa gtgccaacac 38700
tggaccaagc actaagggac aagaatatat aaaaattatt ctccggccgg gtgcggtggc 38760
tcacgcctgt aatcccagca ctttgggagg ccaaggcggg cggatcacaa ggtcaggaga 38820
tcgagaccat cctggctaac acggtgaaac cccgtcttta ctaaaaatac aaaaaaatta 38880
gccgggcgtg gtggtgggcg cctgtagtcc cagctactag gggaggctga ggcaggagaa 38940
tggcgtgaac ctgggaggcg gggcttgcag cgagccgaga tcacgccact gcactccagc 39000
ctgggcgaca gagcaagact ccgtctcaaa aaaaaaaaa aaaaaaaaa ttattctctt 39060
gggaaagct gtctcttgtt ggagacaaac gtatttagaa caaaccttaa tacaagccag 39120
ctccatgtca tgtgccaata aagatgtaaa cagtttggga ttagaaagaa taattgaaag 39180
gtataagttt ttctaattct aggatttgaa acacacgtat tttaattggc taatttaaa 39240
aaaaaaaaa atacaatggg ccaggcgcgg tggctcacgc ctgtaatccc agcactttgg 39300
gaggccgagg cggacgaatc acgagtcag gagatcgaga ccatcctggt taacacggtg 39360
aggacccgcc gtctctacta aaaattcaaa aaattagccg gcatggtgg caggcgcctg 39420
tggtcccagc tgctcgggag gctgaggcag gagaatggtg tgaacccggg aggtggagct 39480
ggcagtcagc agagatcgcg ccactgcact ctagcctggg cgacagagtg agactccatc 39540
tccaaaaaaa aaaaaaaaa aaaaaaaacc tatttgggaa ttgtttgaaa tacttcttat 39600
ttctattaca gctgctggta atagattcct gtaatttgaa ttgatgctga taatttgacc 39660
gtttataagt catttgtttt gtgtccacag aaatcaagat gactaccagc tggttcgaaa 39720
attaggccga ggtaaataca gtgaagtatt tgaagccatc aacatcacaa ataatgaaaa 39780
agttgttgtt aaaattctca aggtgagtac aagagataat ttcagaggta tttggaatat 39840
agatttttaa aagtagtttt gaagactttt ttaaaacagc atttaaaagg ttttggtgc 39900
caaagcaaat aaataaaatt ttattgtatc ctatgaactc aatagaacaa gttctgctta 39960
tttgacagat cgggaaactg aagcaagaga agtgatttga gttgactcat atagctaggt 40020
tgtggcagag taagggagca aaggtacagt ctcttctctc ccagttattg cctaatactt 40080
atttccttta cttttcatta tataatgagg cttttgtttt caataaataa atcattgcct 40140
ctactttgta aagatgagga gtcacaggac tcgagggga cagacagatg atattagtgc 40200
agctagtcgg gtgtaattgc ccttgcttag gtgatgtgag tggtagggac tgaaacaaac 40260
tgggaaacac atgcctcttc aaaaggagtt agctgcttct cagctgaagc tgatgattgc 40320
```

```
cctgcagtaa tgcaagtcca ttgttgcttg atactctgtt ttgcaaataa aagccagaaa    40380
tttatatttg tatatgaatt ttcctgactt ttaagtgttg gctcaagatt ttaaaaaaac    40440
aatgcacagg ccagatttgg cctctgggag accaatatac aacttttaat ttagttataa    40500
ctatgctgtg cactgtcata tattgggaac ttagcatata gttccttacc acaggaactt    40560
tttcatattt gacactgaaa agtagaagtt tccaaacttt ctcaatttat aacacttata    40620
ctgtctttaa ttttttcacgg tactcctaag tcaagaaata cctcatagtt ctctgtatta    40680
agtagcaagg tccaaatagc taagtaagtt ttgttttttt tattgttttt gttttgtttt    40740
tgagaaggag tctcgctctg tcgcccaggc tggagtgcag tggcgcgatc tcggctcact    40800
gcaacctccg cctcctgggt tcaagcgatt ctcctgcctt agcctcccaa gtagctggga    40860
ctacagatgc acgccagcaa tgcccggcta atttttgtaa ttttaataga gacggggttt    40920
caccatattg gtcaggctgg tctcaaactc ctgacctcag gtgatccgcc cgcctcggcc    40980
tcccaaagtg ctgggattac aggcgtgagc cactgcgcct gcccgctaag tatttatatc    41040
ttagcaactt ggtagccatt taaaaagtta ttcacataaa ttaaaagaaa aaagttaaat    41100
ttgttcttat ataactataa tttgttactg ttgggttatg tagacctgtt gctgcatagc    41160
ttttcaaatg ttgtcattgg ttggacacca ccaccctcat ttcctgtcat tgattttgt    41220 gcagtacttg ctttttacca cagcaactac tgcaaaccca gcttcacaaa aatatgccat    41280
cgcgaggagt ataacacaat ccatcacgag gagtgtaaca caatctaatg ttgaaactac    41340
gaaccacctc aagctggcag tgcacccagt gtctggcaga ttcaacgatg ggttgatgtg    41400
tcttcctcaa aaatgtaaag tgttccacag tattcctgtg cattgctggg gtgcttcaca    41460 tgcccttga gaaccagaga gtttaagtat ttatatctgt cttgaaatat gtagaaagag    41520
aactaggttg gaaatcaaaa catgtgggtg actagccata gtagtccttt taacctagga    41580
catgtttatc catctattaa aaagaatgtt ggctgagcat ggtggcatgt gcctttagtc    41640
gcaggtcctc gagggctaa agtgggagga tcgcttgagc ctggaagttg aaggttgcac    41700
ggatctatga tcaaaccact gcactccagc ctgggcgatg agaatgagac cctgtctcaa    41760
aaaacaaaaa ggatcaaaca caaaattgtg tgtatatata catacgttgg agactggagt    41820
tctttgtgat tgtatggtga tattcatatg gaaaggtata tgatagaatg aggtgatata    41880
ttattattta gagccacatg aaaagcatgc atagtgggtc tacagttcag aagagggtag    41940
tagttaggaa aagctcccag gagctgtctt caggctgaat gggaggagga tttggatagg    42000
tgttgggtgg aagtggtgaa gggaagcagg ctgtagagtg caccaagata agaaagagg    42060 aggagggaaa agtgagagaa atatttcatg tgaaagatgt tatgtgacca tacataggag    42120
ttgaacttgg aaagagagat taagttggcg aaggcctgga aaaataatc tctgcatttc    42180 cttgcagtct taaaattata tgactatctc ttctaggtaa ttgtgagccc ttgatgattt    42240
tgaatgaagg gtgatttaga aagatttttt tcagctcagt cttctaact gtattgtata    42300 ttttactgta actgtgggta ggtggtgtaa gtatagatga atttcctttg taaaccatat    42360
ttaaaatttt taatctcccc tatttaataa gacaaaagtt gcattgatcg cattaaattc    42420
gggcctgagt cagctgcctg gtctgtcaca aaccagcttt ttaagtttat agatttgaag    42480
cattctgtag agtagttttg tcaaccagaa gcttttttt tccactaaaa aaccagcagt    42540
tgggttaatg gaaaacagga ggtaagttgt tgggttagtc tctgcagggt ggaaagatct    42600
cccagataat ataacagttt ataaagatct gaatagttga agcaggaaga gaagacttat    42660
```

-continued

```
attatcttgt ttcttaggta gatattgtat tgggtaagag gtcgtgggtt gaattcaatg  42720
gactacatgg aagtcattag taaaatagct tctgtttatt gggtaccact ttgcattgga  42780
cctgttctaa ctgtggtatg taaatcacta acaggcgagt atagtccctt tcagcagtga  42840
gaaacattta aatgcttttc tgaacactgc acaaccacaa agccaggttt tgagaactgt  42900 caatgttttcc aaaatctgct tgctttctgc tatcatgtgc ttgaggctta agacaaagtt  42960
aaaagaattt atagtattat ttggtagttt ctggacctgg atcatcagcc tggaaagtat  43020
ctaaaaataa atccccgtt tccctctcaa gattttgatt tagtgaatct tggtgggttc  43080
tgtgagtctg tatattaaaa aaatccaggt gattgttggt catcaaactt tagtaaccac  43140
caatcttgtt aatgaagaga tgagatgtac ttaacttcta agagttatat gcagtgcatc  43200
tagtctgagg tgaccaacac cctaggaaaa gacctgcaca gtccagtaca gcaggcacgc  43260
aggccacatg aggctgttaa gcacttgaaa tatggctggg ctgaattgag atatgctgta  43320
agagtaaaat acattagatt tcaagggttt aatacaaaaa aaggtaaaat agattaataa  43380
tttttatatt gatttatatg ttaagatttt agattaataa agtacattaa ttttgtcctt  43440
tttaaaattt tcttgatgtg gctactaaca catttaaaat tacacatgtg gtttgtatta  43500
tatttccttt gggccagcac tgttttagac tattcaggag aaggctttat aatataagcc  43560
caggcacagt ggctcatgcc tataatccca gcactttgga aggccaaggc aggcggatca  43620
tgaggtcagg agttcgagac gatcctgacc aacatgatga aaccctgtct ctactaaaaa  43680
tacaaaaatt agctgggcat ggtggctggc gcctgtaatc ccagctactc gggaggctga  43740
ggcaggagaa ttgcttgaac ccgggaggcg gaagttgcag tgagctgaga tcatgctact  43800
acactccagc ctgggcgaca gagcaagact ctgtctcaaa aaaaaaaaaa ggctttataa  43860
aggaggtgca gtgggaccaa ggccctcctc agaaaaaaat gaaaaggatt ccatactaga  43920
acagatgtgg aaagaatggg taaggacaaa ggaatgttta agatatgctc tgcagaatac  43980
tctttagaat ggagggggttc atttataaga gtattggcac tttgggaggc cgaggcaggc  44040
agatcacgag gtcaggagat cgagaccatc ctggctaaca cggtgaaacc ccgtctctac  44100
taaaaataca aaaattagcc tggcctggtg gcgggtgcct gtagtcccag ctactcggga  44160
ggctgaggca agagaatggc gtgaacccag gaggcggagg ttgcagtgag ccaagattgc  44220
accactgcac tccagcctgg gtgacagagc aagactctgt ctcaaaaaaa aaaaaaaaa  44280 aaaaagagca ttggtgatca ggctagacag ttattattat gttatgtttc agccatattc  44340
cgaaatcttt cgaatacctc atttgattct tgcaacaatc ttatgagatg ggtactcttg  44400
ttactcattt tacacttaat gaaaggctta gagaggttat gtagtttgcc attaacagcc  44460
agcaggtagt aaaggtaggt ttcacattgg gcattgtgac tccaagactc acccttacc  44520 ctcagggttg tgctacacaa agatgttttg gccatccttg ttgttggccc taattagagg  44580
aagaaatgga aagggcccat gtttcatcct aattgataaa agtttgata tactttagta  44640 ttactaacga tttaaattgc tactttgtaa ggttttaaga cattaacatg tttaacatgt  44700
tttaaaacat taacatcaag actgatgatt gaaatgctaa ttctgcagaa gtgtctggtc  44760
tttggaatag aaatcttttt ttctttcaat tcaacatttg taagtacctg cagaatacct  44820
ggcacagtgc taggagaagg attcagagac gaatgtgaca cattttcttc cttcaaggtg  44880
tgctcataag taagccattt atcattttat tattacacta cgtgttgaaa tactctgaaa  44940
aaattttttt tttttttttt tgctgatgta ctttcccct ttcagccagt aaaaaagaag  45000
aaaattaagc gtgaaataaa gattttggag aatttgagag gaggtcccaa catcatcaca  45060
```

```
ctggcagaca ttgtaaaaga ccctgtggtg agtatagtag gtgttagcaa ggcccgccag   45120
agctgagatg gtgttgacc  tggagcacaa ctggcctctt tttgttccct ccccaaccc   45180 tcatcattaa gtcctgcttt gaaagtgctt aatcagatat accatttaac tagcttgggt   45240 cttctttca  aagagacctc cacccacaga ctatttctta ttcttctagg ctaagagact   45300
gatagcactg gaaactgaaa tgtgttaatc cattttgcaa actcaggtcc gatgccgatg   45360
ggcgatgggc gcattgtcgg gctgcctaga gcctggtgag acttcagctc catgtcttct   45420
gtttgaaatc catcccaaaa atgacctaag tgcggtgatg atcagagcgg ggagggcttg   45480
tagcaataga gggtttctta ctactgaggc gaggactgcc aaatttcacc acgcagcatc   45540
cgcaaacatt gtccccatta aagctgtcag ggctattgct aatgtgtgtt tttgtttttg   45600 ttctttccc  ctagtcacga accccgcct  tggtttttga acacgtaaac aacacagact   45660
tcaaggtata atatataacc aactgtttcg ggctagtggg ttttagacc  acatagcctt   45720 tggggatgat gctgttagaa gagcttgctt cgcatttgtt tttaaaaagc ttttcatcct   45780
tacagtgcaa attttaagat agaagaactc ctatataagc agtgcccact ttctgcatct   45840
tgatattttg cccatttgtt taatgttctt tttaatgacc aacacattga cttctcacta   45900
cttagttgac agtttctgct gatgtccaac ctaatgaagg cagtaacaca cgttcactta   45960
ggatctggcc atatggcaat tcgctttaaa caatagtgtt caggaagaaa tatattgtat   46020
gtataaaagt agggactgct tatttcttag gattcctcat aaactgtggg ctatagatct   46080
taaaaggcag ggatcgagga aggataatgt caaattctgc cataacacaa acctctataa   46140
gagatatctc agaattccag tctatccagt ggcctactta tttcacacag ttccaatttt   46200
acagaagaat atagctactc ttttggagta aaagtaaaaa tcttcgattt gccttccac   46260 cagtccagta tccagaatgt tatatattaa taaattagtg aattctgttg cagagatagg   46320
gagaaaggaa gaggaactgc tttagagtca gaatgataat ttcaagaaaa actttgtcag   46380
aagacgttgc taaccattaa agagacgtac ctgtggctgg gcatggtggc tttcgcctgt   46440
agtcctagct actgggaag  ctgaggtagg aggatcgctt gagcccagga gtttgaggtt   46500
gcagtgagtt atgattgcag cacggcactc cagcctgggc agcagagtga ggaccctgtc   46560
tcaaaaaaaa aaaaaaaaa  aaaagatatg tccatgtaaa aaacattctg caactctttg   46620
gaaactggaa aggatacata acagttgttc agagtttact ttccaattgg aacaagaata   46680
gttttgttaa attgactcaa caggtttggt atcatgccat ctgcataccc actggtgatc   46740
tgcagggcca actatgtaag gcaaagatga gttagttccc tactaaggag gcagtatatt   46800
tgccaaaatg cctcttttga gaaggtctga agatacatga aaagcaaact aaattatagg   46860
tgggtgtcag tgcatattaa cgtatctaga tcagtatgtt tctgacagtg gattatagct   46920
tccgcaatat atgtttaagt aattcttcat ttttaagagt tgaagaccca aagtatctct   46980
ttaaagttaa tgtaatgttg gagaaataga gggcagtgaa tggacagatc ttggaacaac   47040
ggtaaatgag ccaagtcttg gtttgaatta ctgtgagtga gggtgaaaaa tgcctttctg   47100
tcagcattat ttcatggctc aaacatttgt ctttaacagc aattgtacca gacgttaaca   47160
gactatgata ttcgatttta catgtatgag attctgaagg taagtgaacc ttgaatacta   47220
aatatttttt aaattggtct tcttttttgt aaatagtcaa ttgatggtag aaaagccagc   47280
agattaactt tgtaaagtat gttgaaagaa gggacctcta tataagtttt taataagtta   47340
atagtatcat acctgtaatc ccagcacttt ggaaggctga ggcaggagga ttgcttgagg   47400
```

-continued

```
ccaggagatc aaaagaccag cctgggtgac atagtgagat ccccatctct acaaaaaaaa  47460
attgtttaat tacctgggca tggtggtgtg cacctgtaag tcccagctac ttgggaggcc  47520
aaggcaggag gattgcttga ggccaggaga tcaagaccag cctgagcaac atagtgagac  47580
cctgtctcta caaaaaattt aaaaattagc tgggtatggt ggcttatgct tgtaattcca  47640
gctacttggg aggctgtgac aggaggatct caggaatttg aggcagcagt gagctatgat  47700
tgttgcacag gctggagtgc agtagcacag agtaagaccc tgtctctaaa tacataaata  47760
aataaaaatt aataataata gtatcagaac ccttgtgcta agggttatgg aatgggtct  47820
agtgggagta taatttagaa caatttgaaa aagggtattt gtaagatagc tgggactgac  47880
cccttaacaa atatttgtaa tttctgtggc ccctatgtaa gttaatatta aattttcaaa  47940
actcgtgaaa acacctgacg tgctagcttc tggtatactt tatctcactt aagagtcagc  48000
aaataaaaca gtaaacttta actcagttct caaagggtaa ttgtcctaag gattgtgtaa  48060
atttctgctt atagatgcta attgaaaatt tacttacatt tctaaagtgg ggtcaccaaa  48120
tatcttgttc ccagtagcca caagatcagc ttcctagaag agagaattgc taaaagttgg  48180
ctaagctttc ttactaaaca agagttgaca taaagcctgc tgttggagcc ttagaaatcc  48240
cctgaggaga ttgtgccagc agagatactt gatctttcca ttggctcatg cagtttgtgg  48300
caagcaaggc tttagaaagt tacagatatg attgcccagc cctgggaact gtaggaaccc  48360
aagttgccct tcaggaagga caagaatttg gccaacaacg tcggctgact gaaaggctgg  48420
gattaacaaa ccccaaagat tatactactc agttcccttt agtttgaggt tggaaacatt  48480
tcagattgga tttgatgacc taaatcaggc attggcaaac ttctttaaag ggccaaatag  48540
taaatatttt aggctttgtg ggccatgtag tgtttgtcac actattcaag tctgctgttg  48600
ttgcacaaga gcaaccataa acaatatgca aacaaatagg catggctatg ttgcaataaa  48660
acattattta caaaagcaga catcaggcca aatttggcct gtggtctgcc aacctctgtt  48720
acagactctt aatggctaaa gaattactgt tcttagaata agaggtttgt agtaaagatc  48780
tgttttcttt ctttgagggg tctgtggaaa taatctagga tctggacaag acagaaaaat  48840
ttgaagtggt gcaatttggg tatactttgg gtcttttagg acagaaaaca tgttgaaaca  48900
actgtgtcag aaaaagatct ctaagctcag agagctgagt ttgcttgact gtgagatcat  48960
gaacaagtct ctgaagcatt gctgtggaag tgactgtgtc ctcagcttga atcccagggg  49020
tattgtgagc ctaaaaggaa aatttacatg gagggaaaag taaaggactc ttacgtatta  49080
ttcaggctaa ctcctttctg acccgttcat cccacaggcc ctggattatt gtcacagcat  49140
gggaattatg cacagagatg tcaagcccca taatgtcatg attgatcatg agcacagaaa  49200
ggtaaagtga taggctgaca agtgttattt atctacatga tgtagctaat tgcccatctt  49260
caacacttta tcccttgtgt tgtcacaggc cctagtacct attcggcagt tgagaaatat  49320
ttggtgaatg aatgtacgaa tttacaagtc aacatgtttg aaccattatt tatattccta  49380
agaatattcc caagaaggaa acatgagtaa agtgggcaaa atgttcatct tctaagcccg  49440
gaaacgtggc ttctcgcctt atttattgag taactggttt cctgagaaac tactttctct  49500
ccatttgcct tcttttttctt acgtgtacag tgtgggtaat aatagccctg caggcgacta  49560
ggtattcgtg agaattaaat gtgcacagtt aagtggacga gatatacaga aaatgctgtt  49620
tctgtttatt ggatgtcata agggccctgt tgtctgcaaa tgcttttaca tgagagctgt  49680
aatggccaca tgctttagca tttcagtttt ttaaggtgac aagctgtgat gacttgcctg  49740
ttgtggtctc tggggaggca ggtgatttat ttatgcaact gaattacttt tagacacaca  49800
```

-continued

```
ccatgtcaga ggcaccaccc tagggctggg gatatgtaag tgaactcaac atacaataaa 49860
tgcttgtctt ttaggagcta catttaggga ggctggtggg atagaaagtt attttgatgt 49920
agaagaaaaa acgaataggg aatggcaaga gggtatttgc agttttaaac cagttataag 49980
ggaaggtttc attggaaagg tgacatttta gagagcactg ggagggaccc agccatgcag 50040
tcttatgaag aaacatgtcc caaggcagag taaatagcaa gtacaaaagc ccttcaggta 50100
aggatatgtt tggcatgttg gaagagcagc agcaaggata aagctgggac agaatgaatg 50160
cggggaaaga aggaggaaat gaaatcaaag aggtaaaacc aaatcatgta aaaccttatt 50220
ggtcattgtt aggccttttc tctgaagata gagagctttt gcatattcta agctttagca 50280
tgttctcact tgaaatttaa aagttaacta cacatttatt agaacagcta aaataaaaaa 50340
tagtgatggt accaagtgct ggcaaaaatg tgaagaaact tgatctctca tacattgctg 50400
gtaggaatgc aaagtttggc attttggaaa atgcttaact attgttttat agttggttgg 50460
tttcttgaaa agctaaacat atgcttacca tacaatcctg cagtggcatt tatctcagag 50520
caacaaaatc ttaggtccac acaaaagcct atatatgaat gcaactatat ttgtaatagc 50580
ttaaaattgg ggggaaaagc tgggtgcagt ggctcacacc tgtaatcatt tgggaggcc 50640 aaggcaggca gatgacgagt tcaggagttc aagaccagcc tggccaacat ggtgaaaccc 50700
tgtctctact aaaaaaatac aaaaattagc cgggcctggt ggcatgcacc tgtaatccca 50760
gctactcagg aggctgaggc aggagaattg cttgaacccc ggaggcggag gttgcagtga 50820
gccgagatcg tgccactgtg ctccagcctg ggtgacagag cgagactgcg tctcaaaaaa 50880
aaaaaaaaaa aaaatggggg aaaagtgccc ttcaatgagg gaatggttaa acaaactggc 50940
atatccatac catataatat tattatgaag tagtatttct cagcaataaa aggaaagaa 51000 gtatgacaca tgcaacaact tggatggatc tcatgcttag tgaaaaaagg cagtctcaaa 51060
aaaagttata tgccaatgac tccattttg tagcattctc aaaatgatag agataaagag 51120 cagagggggtt gccagggtt gggctaacac acaggacatg tgtgtggtga tggaacagtt 51180
ctatatcttg ttgaggagat tatatcaact tacatatgtg atgaaattgc atagaaacac 51240
acacacaaac acatgcgtgc atgtaaaact ggtgaaacct gaataagatc tttctgaatt 51300
gtgccagtgt cagtttcttg atttgatat tgtactgtag ttatgtaaga tgttactatt 51360
aggggaaact gggtaaaggg tgcagagaat ctctactact ttggcaattt cctgtgaatc 51420
tataatctct ccatagcaac ctgaacaatc cttttaaaaa gctgtttata tttattttta 51480
aatatttaat tatttttaaa ataactatta aactatttag tatttattaa actgtttaga 51540
ctagagggca agagtgaaag cagtgagacc agttaggaga aggggctatg gcaatatatc 51600
aaacaagagg tggtggtggc ttggatcggg gcagtggcag tggaggtgat gataatggtc 51660
acaatatgat agaaccttca gaattttttg acagattaaa tgtgaggtct gagggaatca 51720
agaatccagg gtgaatctta agttttggct tgtatgacag gatgagtatc acctttaacc 51780
gaacaggggg agactgagtg gaggtgcttt tgcagggagt aatcaaaggt ttagttttga 51840
gatacaggca gtaaacttag tgccagagca gtccgatgtt tttcctcagg gcctactgct 51900
ggcacttcag atcatggtca tgctatgcac agtgggcaga taagcttgcc tcttaccct 51960 ttttccatgt ttaggatgca ttttggtaaa agctgtattg tatgactttt ctgttatttc 52020
atctatccag caaatatttta ttcattttc tcctgtatac caggcattat gttgaattct 52080
gaaaattaca aaggtgaata aaacagtccc taccctaag gagcttgtcg tccatattga 52140
```

```
aaaagaaagg tagaaaacat aaagagttta ggttctgtta aagaaatata tctaaaattc 52200 aggggggctga aggcaatgat cagacttcat tgagaagctg acttaaatat tccaaaagtt 52260
aaggaaatgc ttaccaatag gattataggc tgggtagtag ggacatttta gtcattgagc 52320
agtttaagaa atttgtaaaa gcacaggtga gattgtgtct tccaggaaca aaatcatgga 52380
gaaagaggtt tgtcaagcta agaagtttta ttttcattct aaaggctata agtagtcagt 52440
ggagggtttt cagtaaagag tgacgtgtct ggtatatttt atcaagagta tgctaatggc 52500
acagtgtggg tagcttagag aaagataaga ttgctcatgg tttattcttt ttcagctacg 52560
actaatagac tggggtttgg ctgagtttta tcatcctggc caagaatata atgtccgagt 52620
tgcttcccga tacttcaaag gtcctgagct acttgtagac tatcaggtaa gaacagaagg 52680
gcaggcacag ttttgatcct gtgtttattt cgcacataat ttaccaaaaa aaaaaaagta 52740
tcattttgtg catttaggta ggccacttaa tgcacattca cagctgtcct ttttatatga 52800
aatgtaaaat ataaatcacc ttaattcatg taccatgact tacattactt ttattgtcat 52860
aatgtcggta gaatatgaat aggttttgcat ttgatcctga cttgagggaa agtagccaaa 52920
gatatgttct ataatcagca gttccagaac tgttttgaat tgtaagctgt tttgttttg 52980 tttttgtttt tgttttgaga cggagtctca ctctgtcgcc caggctgcag tgcagtggca 53040
tgatctcggc tcactgcaag ctccgcctcc caggttcaca ccttctcct gcctcagcct 53100 cccaagtagc tgggactaca ggcacccacc accaccccag ctaattttc ttgtattttt 53160 agtagagact gggtttcact gtgttagcca ggatggtctc gatctcctgc cctcgtgagc 53220
caccacgccc ggccttttgt ttgtttctg aggcagggtt ttgctctgtt gcccaggctg 53280
gagtgcaatg ccatgatcat agctgactgc agccccgaac ttctgggctc aagtgatcct 53340
tccagcttag cctcctgagt agctgggact acaggcgtgc actaccacac ccagctaatt 53400
tttaattttt ttgtgtgtag agagaaagtc tcactatgtt gcccaggctg atctcaaact 53460
cctgggcaca acccatcctc acaccttggc tccccaaagt gctgagatta caggcatgag 53520
ccaccatgcc catcctgtaa ctaagtttaa ccaatcttca gagtaaattc aagaatgttt 53580
tcttgttctt ctgaattgta tactaaataa aaaggtcttc tccccagctc ccccaaaaag 53640
ccttctttct cctcacagaa aaaggagaaa ggaaccaaat taataataga tttgccaagt 53700
gtttaaaaat ctgaagtttt cttgggagta tcttttatgc ccagtctttc caggttatta 53760
tcagttgatt ttaaaagttt cagacttttt gttcttgtag gaatttcttt cttgggtct 53820 taaggctata gccctgagtt caaaaagcat tttatgcata aaaatagttt ttacagtatt 53880
actaataatt gtgaaaaaca gaacactgtc ctattatagg aaaattaaag attgaattct 53940
gaaacattta tgtaataaaa tactaatgat acacattaga tggtctccat gggctaacaa 54000
tttggaggtt tttttttttt tttttcatg taagtgaaga aaacaattca aaatagtatg 54060
tatattagct gagcatagtg gtgtatgcct gtaatcctac ctactcagga ggcctaagcc 54120
caggagttgg aggctgcagt gagctatgat cacgccacta cactccagcc tgggcaacag 54180
agcaagaccc tgtgtcttta aaaaaaaaaa aaaagagcc aggcacagtg gctcacgcct 54240
ataatcccag cacttggaaa ggccaaggca agtggatcac aaggtcagga gctcaagacc 54300
agcctggcca agatggtgaa accctgtctc tactaaaaat acaaaaaaat tagccaggcg 54360
cggtggtggg cgcttgtaat cccagctact caggaggctg aggcagagaa ttgcttgaac 54420
ctgggaagct gagttgcaat gagccaagat cacacccctg cagcctgggc gacagagcaa 54480
gactctgtct caaaaaaaaa aaaaaaagt aaaaattgtt ttaaaaccga gtgaaagatg 54540
```

```
cataaaagaa aaaactaaaa aaaaaactaa aaaaaaaaaa aaaagaaaaa actagccagg  54600
cacggtgggt catgcctgta atcctagcac tttgggaacc tgaggcgagc agatcatgag  54660
gtcaggagtt tgagaccact ggccaacgta gtgaaacccc gtctctacta aaaatacaaa  54720
attagccagg catggtggca cgcgcctgta gtcccagcta gtcaggaggc tgaggcagga  54780
gaattgcttg aacccgggag gcggaggttg tggtgagcca agattgcgcc actgcactcc  54840
agcatgggca gcagagtgag actctgtctc aaaaaaaaa aaaaagaaag actaaaaaga  54900
aatatatgaa gatgttatta gtgttttgat tttgagtcag tggagtgatt tttttttaat  54960
tttaaaaatt aattttttat tttgaagtga caagcctgag gattcacaga taataacagt  55020
gagtttactt ttatgcagat gtacgattat agtttggata tgtggagttt gggttgtatg  55080
ctggcaagta tgatctttcg gaaggagcca ttttccatg gacatgacaa ttatgatcag  55140
gtaatatatg ttatacccat tgaaaaatgt actggcctaa tgcaatgata gccagcactg  55200
cctgtaactt tcagttcact gtttattcag ccaccccgat attgatcctt agattgatgt  55260
ttcgggagct accagcttag cctttttgaaa tcagacattc cccctagtc tttgtcattt  55320 gcattgctta ttttattgtg aagaatacat ataaattgtc atccagatt ttaaaatagg  55380 acattacctt agaattctcc taataaaccc ttatctccaa tatggtgttt tctccaatat  55440
gtgagcccat atgtggtatt tctgtgatcc ttttggctct ttatatgggt tgagttacag  55500
atgtttctta aactaactcc acttccccct tgaagatcaa agggctcttt cattcacaag  55560
aacctggaat gattctagga ccttgtggaa ggtaccattg tcttgttccc tttgagcacc  55620
atgtccaatt ttaatgagtc aaagaataca acctgaattc cattaaagtc aataactctg  55680
tatcaagtgc atgcagtact gaggaataca gaaaaagaa agaatagttt tcttcccctc  55740
agatagttca tagctgatct tgtaagggag tcaaacatac aacaaaatag gttacagtca  55800
taacttcaga gtagaaatgt ggacaaggca caaaaggcag tagtggtgag tagtttgagt  55860
gtgcaatggg agcttcccaa aagaagtgac atcttcaatt gggttttgag gggagaaaaa  55920
taagggttca ccagggtgac atttcaagag gaagaaacca gtttataaag tagtttgctt  55980
tttctaacac tatcacattg agttgaagtc taaactgtta ggaggtagca ttcatacctg  56040
tagacatgat gacccgttta tgtaaattca atcattgtta attgttgatt tgttaatata  56100
atatgcttgt gatatgggtt tttgtctttc tttaatacta gttggtgagg atagccaagg  56160
ttctggggac agaagattta tatgactata ttgacaaata caacattgaa ttagatccac  56220
gtttcaatga tatcttgggc aggtaagtca tgaaacaaaa tatgtgcatc tgtggcttaa  56280
gcactttgag agtgaactgg cactaggat cttcaaaata gttatgtttt ctttgccagc  56340
actgtcagga tgtcagtggt ccagtgccac aggatgctgc attgagcagg cctctgataa  56400
aggcattgga ttgaatggcc ctttattcaa attaacttac aggagtctga tggagggtt  56460 atagctagag gattcctaca aaatgaatgt agattctagt agaagggtta cagttgaggc  56520
aaaaatcaaa atttaccttg cttctttaag tgaaaaacct ctctccaaga gaaagaaatt  56580
gaagtagaaa atgcatgctt taagactgat gtgcaggctg ggcacggtgg ctcatatctg  56640
taatcccaga acttaggag gatcacttga gcccaggagt tggagaccag cctgacaac  56700 ataatgagac cctcgactcc atgcatggtg atgtgtggca gtagtccaga ctactaggaa  56760
gctgaggcag gagcttccct tgagcccagg agggaatgct acagagagca atgaacatgt  56820
ggctgcgctc cagtctgggc aacagagtga gaccctgtct ccaaaaaaaa aaaaaaaaag  56880
```

-continued

```
gctatatgca gacaaccgac tcttaacagt agtgactaga tatagtactt atacacttaa 56940
ccactcaaca ggaggagatg gactttcctg atgcaaaggc ttttgctggc caattggcag 57000
agatgccagg aatatgtgtg gggatgggaa ataggcctgg tgagctcagc cacctgaccc 57060
tccttgctac acagaagcgg tcacgtcctg tcaagtaacc tgaattatgt ttcttaaaat 57120
tgagaggact cagatgtctt ttttcactct agctatgttg tttccagtct ccagttagct 57180
ttgttgtccc actcagtggc agagcggtgc aagactaccc tcttgagttt ggatccctct 57240
ttgcttttgt ctgggctgtt agccactaag aaaaatgtag gaatgaaatg ttgggcttct 57300
gtgcccacgt ggcccatttc tcatgccctc ttttggtcct gcagacactc tcgaaagcga 57360
tgggaacgct ttgtccacag tgaaaatcag caccttgtca gccctgaggc cttggatttc 57420
ctggacaaac tgctgcgata tgaccaccag tcacggctta ctgcaagaga ggcaatggag 57480 caccccctatt tctgtgagtc cagatatcta gcccacagag tttgtgcagg cgcagagtcc 57540
tatagaacag agtcgtaatc ccagctcctg tcagcttgct gcaaagttaa ttcacccaca 57600
ctgagcctca gattcttcca gtggggatag tgatggcaac tacattgcag aattactgga 57660
agaattcttc tgtaacagaa tacatgacac aagagcattc ctaaataaac tcttttcata 57720
ctgtgaggat gacacttctc agtgcctcag tctggaatgg ttgaattaga atacacagcc 57780
ctgtatcttt cctgtcccta gtaatcattc gttggaaaga gctaatgagg cttacaaatc 57840
ttaaaattgt atgaacacct tgacttagat ttgtgagtat agccacctgt gccatcctaa 57900
gtgaaaatac cactgagacc caccccatct gcactgtgat gttagctgca acatgacatt 57960
tttccttcgg tgtgatggtt ttgtactgaa tcatttatac ttttgcccaa tacctgaagc 58020
agatagatag gctgattggg atagagaatg tggtcatagc cctaagctac atggacctat 58080
agctttggcc tacttggtac tgggctgtgg acacactggt aatatattac cgtctttgcc 58140
gagttacagt gtcttgtctc cattaaacct caacaggacc agggcttcat taaattcgct 58200
ctgctataaa taattacctc atctttctac catttgattg aaaggttagc ttttaccaca 58260
gtttgatagg aaagctattt ctgcttttta ccacttgtct aattcatggt gaaggcaatt 58320
gccaccttaa gttctttggg gaataatgta gagtatatat aaattgcaaa gaatgaagct 58380
ggctgctttc aggcttccag accattagtt taatctttca agcaaaacag aacctagcct 58440
ttttgtctct tttctagaca ctgttgtgaa ggaccaggct cgaatgggtt catctagcat 58500 gccaggggc agtacgcccg tcagcagcgc caatatgatg tcaggtcagt tcattggtaa 58560 atttttcttta aaaaaatgtg gaagtcaatt actgttctta gctttgtggt ctgatttctt 58620
gtataccttc tcttctccgt actggtggcc ttgtgacttt tttttaacca ggtttcagca 58680
tgcttgacat ttggtatact ttagtgatac tgtcttgagt agggtatccc cttctaggct 58740
agaatctcag cattcctggc tgaaaatttt tggcataggg gcttgaaagt gccaagccat 58800
gaaaaggaaa aatacaccat ttcatcttat agtttgaaat gacagtagtt acatggccct 58860
tagaaacaat gttaagaaat ggggtataga ggtggggttt atacataggt gtgtatgtgt 58920
acaaggacag ttccgtgaca tgtgccagag caactataga gtgcctatca gttgtaaaaa 58980
cataagtaaa atggttttcc attattggat cattgtgacg cacagtgaat ttttatagag 59040
tacccagtta ttccaaagga actacaggca catagcataa gaattataca tataggcaac 59100
atccaagtgg gtgcatatct ggtagtgaag gcatttactt acatatcctc aaataattgc 59160
tgttgccctc ctctttttta agaaaagaac taactgcctt ctagaattta ccccttgagt 59220
atcctacctc tgtacagagt aatgtatatc caaacttact tgtagcctta tttgtaataa 59280
```

-continued

```
caaaacattg agaatagcta tcagtaggaa actggttaaa tcagttatgg tatatccatt   59340
taatggaatg tggtgcagcc agtagaataa gagtttcatg ttctgttaga tctccaactc   59400
caatataata atgtgaaatt taaaacgcaa gatgcagggc caggtgcagt ggctcatgcc   59460
tgtaatccca gcactttggg aggctgaggc gggtgggtca cttgaggtca ggagttcgag   59520
accagcctgg ccagcatggc gaaaccctgt ctctactgga aatacaaaaa attagctggg   59580
cgtggcggcg cgcctttaa tcccagctac ttggaggcta aggcaagata tcgcttgaa    59640 cttgggaggc agaggttgca gtgagccgag atcgcaccgt tgccctccag cctgggtgag   59700
agtgagactc tgtctcaaaa gaaaaagtga gatgcagagc catgtctaag aggagtggga   59760
aagaatgtat aataatgttc tcatatatat atatatatat atatatatat tttttttttt   59820
tttttttttt tttttttttt tttttttttt tttggagaca aggtcttgct ctgtggccaa   59880
ggctggagtg cagtggcaca atctcagctg ctgcagcctc cgcctccgg gttcaagcga   59940 ttctcccacc tcaacctccc aggtagctgg gactacaggc gcccgccatg acgcccagct   60000
aatttttgta tttttagtag agatgggggtt tcaccatgtt ggccaggctg gtcttgaact   60060
cctgacctca ggtgatccgc ccaacttggc ctcccaaagt gctgggcatta caggcgtgag   60120 acactgcacc tggcctttgt atactttttt gaaccttttg tattttgaac catgtgaatg   60180
tattacctgt gtgtacacac acacacacac acacacacac acacaaaaac atgattagag   60240
aggtggaaga aatcaaatgg aaataaattc caaaacacaa ttttatctta gaaaatgctc   60300
tttccccatt caaattgact ttcagtaatt ttgaaagctg ccagctatca agacagcatg   60360
gtgtaagagc acatgagctt tgactgcagt catgtgctgt tcagtatggt agtgactagc   60420
cacgtgaggc tatttaatta caattgaata aaatttaaaa tgtagttcct cagttgcact   60480
agccatattt caagtgctca gcagccacat gtggttggct actggtcacc agggtggaca   60540
tctctgccct agacaggcct gggttagaat ccaaccatgg ttgccacttg cttaatcgtg   60600
tactttggac aaactcctta aattgtccaa gcctagattt cttttacctgt ctcttaaatt   60660 gattaggact tgccacttta acttgaattt gtgagggtca gacttgaagt atatgtaaaa   60720
atccagctaa gaggaagtct tcagtaaaga attattgtgt tccttttgca gtgagtgcta   60780
tgagaaactg gtaagattgc catggttggt gtctttggct cactgacagc tcttttcttt   60840
cagggatttc ttcagtgcca accccttcac cccttggacc tctggcaggc tcaccagtga   60900
ttgctgctgc caaccccctt gggatgcctg ttccagctgc cgctggcgct cagcagtaac   60960
ggccctatct gtctcctgat gcctgagcag aggtggggga gtccaccctc tccttgatgc   61020
agcttgcgcc tggcggggag gggtgaaaca cttcagaagc accgtgtctg aaccgttgct   61080
tgtggattta tagtagttca gtcataaaaa aaaaattata ataggctgat tttcttttttt   61140 cttttttttt ttaactcgaa cttttcataa ctcaggggat tccctgaaaa attacctgca   61200
ggtggaatat ttcatggaca aattttttt tctcccctcc caaatttagt tcctcatcac   61260
aaaagaacaa agataaacca gcctcaatcc cggctgctgc atttaggtgg agacttcttc   61320
ccattcccac cattgttcct ccaccgtccc acactttagg gggttggtat ctcgtgctct   61380
tctccagaga ttacaaaaat gtagcttctc aggggaggca ggaagaaagg aaggaaggaa   61440
agaaggaagg gaggacccaa tctataggag cagtggactg cttgctggtc gcttacatca   61500
ctttactcca taagcgcttc agtggggtta tcctagtggc tcttgtggaa gtgtgtctta   61560
gttacatcaa gatgttgaaa atctacccaa aatgcagaca gatactaaaa acttctgttc   61620
```

```
agtaagaatc atgtcttact gatctaaccc taaatccaac tcatttatac tttatttttt    61680
agttcagttt aaaatgttga taccttccct cccaggctcc ttaccttggt cttttccctg    61740
ttcatctccc aacatgctgt gctccatagc tggtaggaga gggaaggcaa atctttctt    61800 agttttcttt gtcttggcca ttttgaattc atttagttac tgggcataac ttactgcttt    61860
ttacaaaaga aacaaacatt gtctgtacag gtttcatgct agagctaatg ggagatgtgg    61920
ccacactgac ttccatttta agctttctac cttcttttcc tccgaccgtc cccttccctc    61980
acatgccatc cagtgagaag acctgctcct cagtcttgta aatgtatctt gagaggtagg    62040
agcagagcca ctatctccat tgaagctgaa atggtagacc tgtaattgtg ggaaaactat    62100
aaactctctt gttacagccc cgccacccct tgctgtgtgt atatatataa tactttgtcc    62160
ttcatatgtg aaagatccag tgttggaatt ctttggtgta aataaacgtt tggttttatt    62220
tatcaaggtt agatttaagt tccctgtgta aaggtcttgc tgggtgggtg tctcatgttc    62280
acatctgagg ggcctgcagc cctgtaccgt ggaggcttcc caaggcccc attttatca    62340 cccctcgttc gacccatggt accgggcaga gcagagaggc cttaaaaaaa agcaccaca    62400 agccaaagcg tctctgggga ttaaggatcc tttgccataa aactcatttt gtgtctcagc    62460
agtgcaggga ttgggatgg aaaagtcgc cagtttttgt gtgtttgtgt gtgtgtaa    62520 agtggacttt ccactgtaat ccaaccacct aagtttatca ggtgcttcac tgaggaagcc    62580
tagtttttta agcacaatag caaaaccatc agctctgtat ttctcctgt tatttcatta    62640 cagtagctgc ttgtgggaac taggaaaaat tcttccaaca tattttaagg cctaaaatct    62700
tagttcccca ttctcctacc ttatagattc acaggccttt ctcgcctagg catcatagat    62760
aaacgtaatt gtttggggag ttgaatttaa tgaacttatc taactttgta acccatcttg    62820
gctttagtaa ctttatcaag gtggtggctt tagtgaatat aatggtaaac tttagaggac    62880
gctaaagcct ccttttatag cgcttctcaa cggtagggag agctgaaggg aaacattct    62940 gactgtgtgg cagggtgatt ttcttcctta tgaccactta cagtggatat ttattgtact    63000

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gggtcccgac atgtcagaca                                                 20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ccccattcca ccacatgtga                                                 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
```
catgatcaat catgacatta                      20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gaagcaactc ggacattata                      20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
actgatcata attgtcatgt                      20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
aaccttggct atcctcacca                      20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ggatctaatt caatgttgta                      20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
gagtgtctgc ccaagatatc                      20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
acaaagcgtt cccatcgctt                      20

<210> SEQ ID NO 28
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 28
ggtgagcctg ccagaggtcc                                               20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ttcttcaaac tgtggtggaa                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tttttactgg cttgagaatt                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
acaacagtgt agaaataggg                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gaaatccctg acatcatatt                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
ccacattcct tctctgtggt                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
gggaaattca cttccaagct                                               20
```

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gccaaaaatc aagtgtctc                                           20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gccttgatag aggtaggtca                                          20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
gacaagcctt gatagaggta                                          20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
atgatttacc atgtgatgag                                          20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tcagacctgt tttcttcaaa                                          20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
atgtttggag atctggcagt                                          20

<210> SEQ ID NO 41
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 41
ggacaaagct ggacttgatg                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
caggttggcg gacaaagctg                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
cccgacatgt cagacaggtt                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
tggcacgggt cccgacatgt                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
tgcttggcac gggtcccgac                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
tggccctgct tggcacgggt                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gtgtaaactc tggccctgct                                               20

```
<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
acaacaactt tttcattatt                                             20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ttttaacaac aacttttca                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50 gagaattta acaacaactt                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
aatctttatt tcacgcttaa                                             20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
aaattctcca aaatctttat                                             20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53 gggtcttta caatgtctgc                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 54
tcgtgacaca gggtctttta                                               20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
attgcttgaa gtctgtgttg                                               20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
gtacaattgc ttgaagtctg                                               20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gtctggtaca attgcttgaa                                               20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ttaacgtctg gtacaattgc                                               20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
gtctgttaac gtctggtaca                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
tttctgtgct catgatcaat                                               20

<210> SEQ ID NO 61
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 61
atcctcacca actgatcata                                                  20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
tagtcatata aatcttctgt                                                  20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ttcactgtgg acaaagcgtt                                                  20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
cgtgactggt ggtcatatcg                                                  20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cctggtcctt cacaacagtg                                                  20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
atcatattgg cgctgctgac                                                  20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
```

-continued aatccctgac atcatattgg                    20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
gcactgaaga aatccctgac                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tcactggtga gcctgccaga                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
tagggccgtt actgctgagc                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
cctctgctca ggcatcagga                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ccacctctgc tcaggcatca                    20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ggcgcaagct gcatcaagga                    20

<210> SEQ ID NO 74
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 74
ctgaagtgtt tcacccctcc                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
acacggtgct tctgaagtgt                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
aacggttcag acacggtgct                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
aatccacaag caacggttca                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ctgcaggtaa tttttcaggg                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ggaatgggaa gaagtctcca                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
accaaccccc taaagtgtgg                                               20
```

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
ctcctataga ttgggtcctc                                                   20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
tcttactgaa cagaagtttt                                                   20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
atttagggtt agatcagtaa                                                   20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
tatgcccagt aactaaatga                                                   20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
tgaaacctgt acagacaatg                                                   20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
acatctccca ttagctctag                                                   20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 87
gtgtggccac atctcccatt                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
tgtaacaaga gagtttatag                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
caaaagtttc caagtaatga                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
agtattcttt ctaaaggtct                                              20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
gtgttttcaa agtctctcaa                                              20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
caggcctctt tgaaggtaaa                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
gactacaggc gaaagccacc                                              20

<210> SEQ ID NO 94
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
cccacaaagc ctaaaatatt                                                     20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
cattcaccaa atatttctca                                                     20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
tgacatcctg acagtgctgg                                                     20
```

ANTISENSE INHIBITION OF CASEIN KINASE 2-ALPHA EXPRESSION

FIELD OF THE INVENTION

The present invention provides compositions and methods for modulating the expression of Casein kinase 2-alpha. In particular, this invention relates to compounds, particularly oligonucleotides, specifically hybridizable with nucleic acids encoding Casein kinase 2-alpha. Such compounds have been shown to modulate the expression of Casein kinase 2-alpha.

BACKGROUND OF THE INVENTION

The process of phosphorylation, defined as the attachment of a phosphate moiety to a biological molecule through the action of enzymes called kinases, represents a major course by which intracellular signals are propagated resulting finally in a cellular response. Within the cell, these enzymes are generally classified into a protein-serine/threonine subfamily or a protein-tyrosine subfamily on the basis of phosphorylation substrate specificity. The extent of protein phosphorylation, in turn, is regulated by the opposing action of phosphatases which remove the phosphate moieties. Because phosphorylation is such a ubiquitous process within cells and because cellular phenotypes are largely influenced by the activity of these pathways, it is currently believed that a number of disease states and/or disorders are a result of either aberrant activation of, or functional mutations in, kinases. Consequently, considerable attention has been devoted to the study of kinases and their role in disease processes.

The protein kinases comprise an exceptionally large family of eukaryotic proteins which mediate the responses of cells to external stimuli and to date, in excess of several hundred unique members of the protein kinase family from a wide variety of eukaryotic organisms have been described and characterized at the amino acid sequence level.

Among the enzymes within the protein-serine/threonine kinase subfamily are two distinct casein kinases which have been designated casein kinase I (CKI) and casein kinase II (CKII or CK2) identified by the order of their elution from DEAE-cellulose. The casein kinases are distinguished from other protein kinases by their ability to phosphorylate serine or threonine residues within acidic recognition sequences such as found in casein and each has been thoroughly characterized regarding their physicochemical properties, recognition sequences, substrate specificity and effects on metabolic regulation. These enzymes have been found throughout the cell and their activities have been purified from or found to be associated with cytoplasmic fractions, membranes, nuclei, mitochondria, and cytoskeleton reviewed in (Tuazon and Traugh, *Adv. Second Messenger Phosphoprotein Res.*, 1991, 23, 123–164).

Casein kinase 2 (also known generally as casein kinase as well as CKII, CK2 and CSNK2) is a heterotetrameric holoenzyme composed of two catalytic (alpha and/or alpha prime (alpha')) subunits (Lozeman et al., *Biochemistry*, 1990, 29, 8436–8447; Meisner et al., *Biochemistry*, 1989, 28, 4072–4076) and two regulatory beta subunits (Heller-Harrison et al., *Biochemistry*, 1989, 28, 9053–9058; Jakobi et al., *Eur. J. Biochem.*, 1989, 183, 227–233). While the alpha subunits contain the enzyme's active site, the non-catalytic beta subunit functions to protect the alpha subunit against denaturing agents or conditions and alters the substrate specificity of the enzyme. The alpha subunit protein has also been shown to activate transcription of the beta subunit gene (Robitzki et al., *J. Biol. Chem.*, 1993, 268, 5694–5702).

Casein kinase 2 is unique in that it recognizes phosphoacceptor sites specified by several acidic determinants, it can use both ATP and GTP as phosphoryl donors, it is insensitive to any known second messenger and displays high basal activity.

Casein kinase 2 is constitutively active, highly pleiotropic and its targeting seems to be modulated through association with a variety of cellular proteins, more than 160 of which are known (Pinna and Meggio, *Prog. Cell Cycle Res.*, 1997, 3, 77–97). Its expression is abnormally elevated in proliferating and neoplastic tissues and recent studies suggest that mice overexpressing the alpha subunit of casein kinase 2 develop leukemia. Several compounds have been shown to affect the activity of casein kinase 2 with polycationic species stimulating activity and polyanionic species acting as inhibitors (Pinna, *Biochim. Biophys. Acta*, 1990, 1054, 267–284).

Physiologically, casein kinase 2 has been shown to play a role in cell cycle progression (Marshak and Russo, *Cell. Mol. Biol. Res.*, 1994, 40, 513–517), liver regeneration (Perez et al., *FEBS Lett.*, 1988, 238, 273–276), viral replication (Dupuy et al., *J. Virol.*, 1999, 73, 8384–8392; Lenard, *Pharmacol. Ther.*, 1999, 83, 39–48; Schubert et al., *J. Mol. Biol.*, 1994, 236, 16–25; Wadd et al., *J. Biol. Chem.*, 1999, 274, 28991–28998), apoptosis (Watabe et al., *Cell. Growth Differ.*, 1997, 8, 871–879), transduction of growth signals (Tawfic and Ahmed, *J. Biol. Chem.*, 1994, 269, 24615–24620), prostate cancer (Yenice et al., *Prostate*, 1994, 24, 11–16), breast cancer (O'Brien et al., *Biochem. Biophys. Res. Commun.*, 1999, 260, 658–664), insulin signaling (Singh, *Mol. Cell. Biochem.*, 1993, 121, 167–174) and Alzheimer's disease (Blanquet, *Neuroscience*, 1998, 86, 739–749).

Inhibitors of the enzyme, as a whole or subunit-specific, may have therapeutic potential and consequently, modulation of casein kinase 2 activity and/or expression is believed to be an appropriate point of therapeutic intervention in pathological conditions.

To date, investigative strategies aimed at modulating casein kinase 2 function have involved the use of antibodies, antisense oligonucleotides, and chemical inhibitors.

Disclosed in U.S. Pat. No. 5,171,217 are methods of delivering inhibitors of protein kinases, including casein kinase 2, to an affected intramural site (March et al., 1992).

Antisense oligonucleotides targeting each of the subunits of casein kinase 2 in various organisms have been reported in the art. Chen et al. designed one antisense oligonucleotide targeting the beta subunit of casein kinase 2 in Xenopus to investigate oocyte maturation (Chen and Cooper, *Proc. Natl. Acad. Sci. U. S. A.*, 1997, 94, 9136–9140). This oligonucleotide targeted residues 175–182 and contained phosphodiester links with the three phosphodiester links at the 3' end replaced by phosphorothioate links.

Shayan et al. report the use of an antisense oligonucleotide targeting the alpha subunit of casein kinase 2 in viral infected bovine lymphoblastoid cells (Shayan and Ahmed, *Parasitol. Res.*, 1997, 83, 526–532). In the mouse, antisense oligonucleotides targeting the start codon of each of the three subunits have been designed and used to investigate the process of neuritogenesis (Ulloa et al., *Embo J.*, 1993, 12, 1633–1640; Ulloa et al., *Cell. Mol. Neurobiol.*, 1994, 14, 407–414).

Antisense oligonucleotides, targeting the start codon of each of the subunits of human casein kinase 2, have also been reported (Pepperkok et al., *Exp. Cell. Res.*, 1991, 197, 245–253; Pyerin et al., *Ann. N. Y. Acad. Sci.*, 1992, 660, 295–297). In these studies of human fibroblasts (IMR-90 cells), antisense oligonucleotides were used to investigate the role of casein kinase 2 in early growth stimulation by epidermal growth factor (Pepperkok et al., *Exp. Cell. Res.*, 1991, 197, 245–253; Pyerin et al., *Ann. N. Y. Acad. Sci.*, 1992, 660, 295–297).

In MDA231 breast carcinoma cell lines, an antisense oligonucleotide targeting the start codon of the alpha prime subunit of human casein kinase 2 was used to investigate alternative splicing patterns in the CD44 gene (Formby and Stern, *Mol. Cell. Biochem.*, 1998, 187, 23–31). And in human Ca9–22 cells derived from squamous cell carcinomas of the head and neck (SCCHN), transfection with a phosphodiester antisense oligonucleotide targeting the alpha subunit of human casein kinase 2 resulted in growth inhibition of the carcinoma cell line (Faust et al., *Head Neck*, 2000, 22, 341–346).

Antisense technology is emerging as an effective means for reducing the expression of specific gene products and may therefore prove to be uniquely useful in a number of therapeutic, diagnostic, and research applications for the modulation of casein kinase 2 expression.

The present invention provides compositions and methods for modulating the expression of the alpha subunit of casein kinase 2.

SUMMARY OF THE INVENTION

The present invention is directed to compounds, particularly antisense oligonucleotides, which are targeted to a nucleic acid encoding Casein kinase 2-alpha, and which modulate the expression of Casein kinase 2-alpha. Pharmaceutical and other compositions comprising the compounds of the invention are also provided. Further provided are methods of modulating the expression of Casein kinase 2-alpha in cells or tissues comprising contacting said cells or tissues with one or more of the antisense compounds or compositions of the invention. Further provided are methods of treating an animal, particularly a human, suspected of having or being prone to a disease or condition associated with expression of Casein kinase 2-alpha by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding Casein kinase 2-alpha, ultimately modulating the amount of Casein kinase 2-alpha produced. This is accomplished by providing antisense compounds which specifically hybridize with one or more nucleic acids encoding Casein kinase 2-alpha. As used herein, the terms "target nucleic acid" and "nucleic acid encoding Casein kinase 2-alpha" encompass DNA encoding Casein kinase 2-alpha, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Casein kinase 2-alpha. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Casein kinase 2-alpha. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Casein kinase 2-alpha, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U. S. A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses.

Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al., *Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of Casein kinase 2-alpha is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Casein kinase 2-alpha, enabling sandwich and other assays to easily be constructed to exploit this fact. Hybridization of the antisense oligonucleotides of the invention with a nucleic acid encoding Casein kinase 2-alpha can be detected by means known in the art. Such means may include conjugation of an enzyme to the oligonucleotide, radiolabelling of the oligonucleotide or any other suitable detection means. Kits using such detection means for detecting the level of Casein kinase 2-alpha in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable.

Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyamines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyamines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. Nos. 08/886,829 (filed Jul. 1, 1997), 09/108,673 (filed Jul. 1, 1998), 09/256, 515 (filed Feb. 23, 1999), 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms,* Lieberman, Rieger and Banker (Eds.), 1988, Marcel Dekker, Inc., New York, N.Y., volume 1, p. 199; Rosoff, in *Pharmaceutical Dosage Forms,* Lieberman, Rieger and Banker (Eds.), 1988, Marcel Dekker, Inc., New York, N.Y., Volume 1, p. 245; Block in *Pharmaceutical Dosage Forms,* Lieberman, Rieger and Banker (Eds.), 1988, Marcel Dekker, Inc., New York, N.Y., volume 2, p. 335; Higuchi et al., in *Remington's Pharmaceutical Sciences,* Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms,* Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms,* Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms,* Lieberman, Rieger and Banker (Eds.), 1988, Marcel Dekker, Inc., New York, N.Y., volume 1, p. 335; Idson, in *Pharmaceutical Dosage Forms,* Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms,* Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms,* Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms,* Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems,* Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences,* Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms,* Lieberman, Rieger and Banker (Eds.), 1988, Marcel Dekker, Inc., New York, N.Y., volume 1, p. 245; Block, in *Pharmaceutical Dosage Forms,* Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research,* 1994, 11, 1385–1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research,* 1994, 11, 1385; Ho et al., *J. Pharm. Sci.,* 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms,* Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting,* 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.,* 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.,* 1980, 53, 2778) described liposomes comprising a nonionic detergent, $2C_{12}15G$, that contains a PEG moiety. Illum et al. (*FEBS Lett.,* 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.,* 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta,* 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms,* Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms,* Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me—C) nucleotides were synthesized according to published methods [Sanghvi, et. al., Nucleic Acids Research, 1993, 21, 3197–3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., J. Med. Chem., 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., Helvetica Chimica Acta, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3,-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1 M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'- dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P$_2$O$_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 Al 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine To 0.5 g (1.3 mmol) of 2'-O-[2(2-N,N-dimethylaminoethoxy)ethyl]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O—Me]-[2'-deoxy]-[2'-O—Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl) amidites for the 2'-0-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 5 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

b.END Cells

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds

When cells reached 80% confluency, they were treated with oligonucleotide. For cells grown in 96-well plates, wells were washed once with 200 µL OPTI-MEM™-1 reduced-serum medium (Gibco BRL) and then treated with 130 µL of OPTI-MEM™-1 containing 3.75 µg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Casein kinase 2-alpha Expression

Antisense modulation of Casein kinase 2-alpha expression can be assayed in a variety of ways known in the art. For example, Casein kinase 2-alpha mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., Current Protocols in Molecular Biology, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of Casein kinase 2-alpha can be quantitated in a variety of ways well known in the art, such as immunoprecipitation, Western blot analysis (immunoblotting), ELISA or fluorescence-activated cell sorting (FACS). Antibodies directed to Casein kinase 2-alpha can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1–11.12.9, John Wiley & Sons, Inc., 1997. Preparation of monoclonal antibodies is taught in, for example, Ausubel, F. M. et al., Current Protocols in Molecular Biology, Volume 2, pp. 11.4.1–11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1–10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1–11.2.22, John Wiley & Sons, Inc., 1991.

Example 11

Poly(A)+ mRNA Isolation

Poly(A)+ mRNA was isolated according to Miura et al., Clin. Chem., 1996, 42, 1758–1764. Other methods for poly(A)+ mRNA isolation are taught in, for example, Ausubel, F. M. et al., Current Protocols in Molecular Biology, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate was vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Casein Kinase 2-alpha mRNA Levels

Quantitation of Casein kinase 2-alpha mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1×TAQMAN™ buffer A, 5.5 mM $MgCl_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 µL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human Casein kinase 2-alpha were designed to hybridize to a human Casein kinase 2-alpha sequence, using published sequence information (GenBank accession number 1593_041B, incorporated herein as SEQ ID NO:3). For human Casein kinase 2-alpha the PCR primers were: forward primer: CTCAGCAGTAACGGC-CCTATCT (SEQ ID NO: 4) reverse primer: CGCAAGCT-GCATCAAGGA (SEQ ID NO: 5) and the PCR probe was: FAM-CTCCTGATGCCTGAGCAGAGGTGGG-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: GAAGGTGAAGGTCGGAGTC (SEQ ID NO: 7) reverse primer: GAAGATGGTGATGGGATTTC (SEQ ID NO: 8) and the PCR probe was: 5' JOE-CAAGCTTCCCGTTCTCAGCCX-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse Casein kinase 2-alpha were designed to hybridize to a mouse Casein kinase 2-alpha sequence, using published sequence information (GenBank accession number U51866, incorporated herein as SEQ ID NO:10). For mouse Casein kinase 2-alpha the PCR primers were: forward primer: TCCACAGTGAAAACCAGCATCT (SEQ ID NO:11) reverse primer: GGTGGTCATATC-GAAGCAGCTT (SEQ ID NO: 12) and the PCR probe was: FAM-TCCAGAAAATCCAAGGCCTCAGGGCT-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were: forward primer: GGCAAATTCAACGGCACAGT (SEQ ID NO: 14) reverse primer: GGGTCTCGCTCCTGGAAGAT (SEQ ID NO: 15) and the PCR probe was: 5' JOE-AAGGCCGAGAATGGGAAGCTTGTCATCX-TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Casein Kinase 2-alpha mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human Casein kinase 2-alpha, a human Casein kinase 2-alpha specific probe was prepared by PCR using the forward primer CTCAGCAGTAACGGCCCTATCT (SEQ ID NO: 4) and the reverse primer CGCAAGCTG-CATCAAGGA (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse Casein kinase 2-alpha, a mouse Casein kinase 2-alpha specific probe was prepared by PCR using the forward primer TCCACAGTGAAAACCAGCATCT (SEQ ID NO:11) and the reverse primer GGTGGT-CATATCGAAGCAGCTT (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Casein Kinase 2-alpha Expression by Chimeric Phosphorothioate Oligonucleotides Having 2'-MOE Wings and a Deoxy Gap In accordance with the present invention, a series of oligonucleotides were designed to target different regions of the human Casein kinase 2-alpha RNA, using published sequences (a concatenation of all human casein kinase 2-alpha exons excised from the complement of GenBank accession number AL049761.10, incorporated herein as SEQ ID NO: 3, GenBank accession number M55265, incorporated herein as SEQ ID NO: 17, and residues 21211–84210 of the complement of GenBank accession number AL049761.10, incorporated herein as SEQ ID NO: 18). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human Casein kinase 2-alpha mRNA levels by quantitative real-time PCR as described in other examples herein. Data are averages from two experiments. If present, "N.D." indicates "no data".

TABLE 1

Inhibition of human Casein kinase 2-alpha mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 123336 | Start Codon | 3 | 499 | gggtcccgacatgtcagaca | 68 | 19 |
| 123339 | Coding | 3 | 588 | ccccattccaccacatgtga | 72 | 20 |
| 123346 | Coding | 3 | 986 | catgatcaatcatgacatta | 60 | 21 |
| 123348 | Coding | 3 | 1068 | gaagcaactcggacattata | 61 | 22 |
| 123350 | Coding | 3 | 1211 | actgatcataattgtcatgt | 58 | 23 |
| 123351 | Coding | 3 | 1231 | aaccttggctatcctcacca | 79 | 24 |
| 123353 | Coding | 3 | 1287 | ggatgtaattcaatgttgta | 74 | 25 |
| 123354 | Coding | 3 | 1317 | gagtgtctgcccaagatatc | 70 | 26 |
| 123355 | Coding | 3 | 1341 | acaaaccgttcccatcgctt | 80 | 27 |
| 123361 | Coding | 3 | 1599 | ggtgagcctgccagaggtcc | 92 | 28 |
| 127145 | 5'UTR | 17 | 29 | ttcttcaaactgtggtggaa | 36 | 29 |
| 127146 | Coding | 17 | 352 | tttttactggcttgagaatt | 64 | 30 |
| 127147 | Coding | 17 | 1112 | acaacagtgtagaaataggg | 12 | 31 |
| 127148 | Coding | 17 | 1196 | gaaatccctgacatcatatt | 55 | 32 |
| 127149 | 5'UTR | 3 | 33 | ccacattccttctctgtggt | 31 | 33 |
| 127150 | 5'UTR | 3 | 158 | gggaaattcacttccaagct | 80 | 34 |
| 127151 | 5'UTR | 3 | 203 | gccaaaaatcaaggtgtctc | 86 | 35 |
| 127152 | 5'UTR | 3 | 273 | gccttgatagaggtaggtca | 5 | 36 |
| 127153 | 5'UTR | 3 | 278 | gacaagccttgatagaggta | 70 | 37 |
| 127154 | 5'UTR | 3 | 308 | atgatttaccatgtgatgag | 73 | 38 |
| 127155 | 5'UTR | 3 | 398 | tcagacctgttttcttcaaa | 83 | 39 |
| 127156 | 5'UTR | 3 | 455 | atgtttggagatgtggcagt | 53 | 40 |
| 127157 | 5'UTR | 3 | 472 | ggacaaagctggacttgatg | 60 | 41 |
| 127158 | 5'UTR | 3 | 481 | caggttggcggacaaagctg | 68 | 42 |

TABLE 1-continued

Inhibition of human Casein kinase 2-alpha mRNA levels by
chimeric phosphorothioate oligonucleotides having 2'-MOE
wings and a deoxy gap

| ISIS # | REGION | TARGET SEQ ID NO | TARGET SITE | SEQUENCE | % INHIB | SEQ ID NO |
|---|---|---|---|---|---|---|
| 127159 | Start Codon | 3 | 495 | cccgacatgtcagacaggtt | 70 | 43 |
| 127160 | Start Codon | 3 | 505 | tggcacgggtcccgacatgt | 69 | 44 |
| 127161 | Start Codon | 3 | 509 | tgcttggcacgggtcccgac | 67 | 45 |
| 127162 | Coding | 3 | 515 | tggccctgcttggcacgggt | 75 | 46 |
| 127163 | Coding | 3 | 525 | gtgtaaactctggccctgct | 79 | 47 |
| 127164 | Coding | 3 | 687 | acaacacattttcattatt | 61 | 48 |
| 127165 | Coding | 3 | 692 | ttttaacaacaacttttca | 69 | 49 |
| 127166 | Coding | 3 | 697 | gagaattttaacaacaactt | 59 | 50 |
| 127167 | Coding | 3 | 739 | aatctttatttcacgcttaa | 75 | 51 |
| 127168 | Coding | 3 | 750 | aaattctccaaaatctttat | 48 | 52 |
| 127169 | Coding | 3 | 798 | gggtcttttacaatgtctgc | 67 | 53 |
| 127170 | Coding | 3 | 808 | tgctgacacgggtcttttta | 82 | 54 |
| 127171 | Coding | 3 | 857 | attgcttgaagtctgtgttg | 72 | 55 |
| 127172 | Coding | 3 | 862 | gtacaattgcttgaagtctg | 59 | 56 |
| 127173 | Coding | 3 | 967 | gtctggtacaattgcttgaa | 84 | 57 |
| 127174 | Coding | 3 | 872 | ttaacgtgtggtacaattgc | 82 | 58 |
| 127175 | Coding | 3 | 877 | gtctgttaacgtctgctaca | 73 | 59 |
| 127176 | Coding | 3 | 996 | tttctgtgctcatgatcaat | 64 | 60 |
| 127177 | Coding | 3 | 1221 | atcctcaccaactgctcata | 48 | 61 |
| 127178 | Coding | 3 | 1257 | tagtcatataaatcttctgt | 72 | 62 |
| 127179 | Coding | 3 | 1351 | ttcactgtggacaaagcgtt | 82 | 63 |
| 127180 | Coding | 3 | 1422 | cgtgactggtggtcatatcg | 73 | 64 |
| 127181 | Coding | 3 | 1481 | cctggtccttcacaacagtg | 82 | 65 |
| 127182 | Coding | 3 | 1542 | atgatattggcgctgctgac | 79 | 66 |
| 127183 | Coding | 3 | 1552 | aatccctgacatcatattgg | 73 | 67 |
| 127184 | Coding | 3 | 1562 | gcagtcaagaaatccctgac | 89 | 68 |
| 127185 | Coding | 3 | 1604 | tcactggtgagcctgccaga | 70 | 69 |
| 127186 | Stop Codon | 3 | 1671 | tagggccgttactgctgagc | 87 | 70 |
| 127187 | 3'UTR | 3 | 1697 | cctctgctcaggcatcagga | 92 | 71 |
| 127188 | 3'UTR | 3 | 1700 | ccacctctgctcacccatca | 78 | 72 |
| 127189 | 3'UTR | 3 | 1734 | ggcgcaagctgcatcaagga | 85 | 73 |
| 127190 | 3'UTR | 3 | 1760 | ctgaagtgtttcacccctcc | 76 | 74 |
| 127191 | 3'UTR | 3 | 1771 | acacggtgcttctgccgtgt | 74 | 75 |
| 127192 | 3'UTR | 3 | 1781 | aacggttcagacacggtgct | 80 | 76 |
| 127193 | 3'UTR | 3 | 1792 | aatccacaagcaacggttca | 84 | 77 |
| 127194 | 3'UTR | 3 | 1905 | ctgcaggtaattttcaggg | 59 | 78 |
| 127195 | 3'UTR | 3 | 2031 | ggaatgggaagaagtctcca | 79 | 79 |
| 127196 | 3'UTR | 3 | 2072 | accaaccccctaaagtgtgg | 73 | 80 |
| 127197 | 3'UTR | 3 | 2174 | ctcctatagattgggtcctc | 85 | 81 |
| 127198 | 3'UTR | 3 | 2331 | tattactgaacagaagtttt | 60 | 82 |
| 127199 | 3'UTR | 3 | 2359 | atttagggttagatcagtaa | 49 | 83 |
| 127200 | 3'UTR | 3 | 2552 | tatgcccagtaactaaatga | 63 | 84 |
| 127201 | 3'UTR | 3 | 2600 | tgaaacctgtacagacaatg | 90 | 85 |
| 127202 | 3'UTR | 3 | 2622 | acatctcccattagctctag | 83 | 86 |
| 127203 | 3'UTR | 3 | 2630 | gtgtggccacatctcccatt | 75 | 87 |
| 127204 | 3'UTR | 3 | 2820 | tgtaacaagagagttttatag | 75 | 88 |
| 127205 | Intron 3 | 18 | 22406 | caaaagtttccaagtaatga | 38 | 89 |
| 127206 | Intron 3 | 18 | 24982 | agtattctttctaaaggtct | 63 | 90 |
| 127207 | Intron 4 | 18 | 37138 | gtgttttcaaagtctctcaa | 55 | 91 |
| 127208 | Intron 4 | 18 | 38600 | caggcctctttgaaggtaaa | 57 | 92 |
| 127209 | Intron 7 | 18 | 46425 | gactacaggcgaaagccacc | 53 | 93 |
| 127210 | Intron 8 | 18 | 48543 | cccacaaagcctaaaatatt | 20 | 94 |
| 127211 | Intron 9 | 18 | 49311 | cattcaccaaatatttctca | 61 | 95 |
| 127212 | Intron 12 | 18 | 56336 | tgcatcctgacagtgctgg | 55 | 96 |

As shown in Table 1, SEQ ID NOs 19, 20, 21, 22, 23, 24, 25, 26, 27, 28, 30, 32, 34, 35, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 90, 91, 92, 93, 95 and 96 demonstrated at least 40% inhibition of human Casein kinase 2-alpha expression in this assay and are therefore preferred. The target sites to which these preferred sequences are complementary are herein referred to as "active sites" and are therefore preferred sites for targeting by compounds of the present invention.

Example 16

Antisense Inhibition of Mouse Casein Kinase 2-alpha Expression by Chimeric Phosphorothioate Oligonucleotides Having 2'-MOE wings and a Deoxy Gap In accordance with the present invention, a second series of oligonucleotides were designed to target different regions of the mouse Casein kinase 2-alpha RNA, using published sequences (GenBank accession number U51866, incorporated herein as SEQ ID NO: 10). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse Casein kinase 2-alpha mRNA levels by quantitative real-time PCR as described in other examples herein. Data are averages from two experiments. If present, "N.D." indicates "no data".

TABLE 2

Inhibition of mouse Casein kinase 2-alpha mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 123336 | Start Codon | 10 | 196 | gggtcccgacatgtcagaca | 49 | 19 |
| 123339 | Coding | 10 | 285 | ccccattccaccacatgtga | 74 | 20 |
| 123346 | Coding | 10 | 683 | catgatcaatcatgacatta | 64 | 21 |
| 123348 | Coding | 10 | 765 | gaagcaactcggacattata | 75 | 22 |
| 123350 | Coding | 10 | 908 | actgatcataattgtcatgt | 47 | 23 |
| 123351 | Coding | 10 | 928 | aaccttggctatcctcacca | 76 | 24 |
| 123353 | Coding | 10 | 985 | ggatgtaattcaatgttgta | 71 | 25 |
| 123354 | Coding | 10 | 1014 | gagtgtctgcccaagatatc | 60 | 26 |
| 123355 | Coding | 10 | 1038 | acaaaccgttcccatcgctt | 74 | 27 |
| 123361 | Coding | 10 | 1296 | ggtgagcctgccagaggtcc | 67 | 28 |
| 127145 | 5'UTR | 10 | 84 | ttcttcaaactgtggtggaa | 47 | 29 |
| 127146 | Coding | 10 | 407 | tttttactggcttgagaatt | 64 | 30 |
| 127147 | Coding | 10 | 1167 | acaacagtgtagaaataggg | 21 | 31 |
| 127148 | Coding | 10 | 1251 | gaaatccctgacatcatatt | 60 | 32 |
| 127155 | 5'UTR | 10 | 95 | tcagacctgttttcttcaaa | 37 | 39 |
| 127157 | 5'UTR | 10 | 178 | ggacaaagctggacttgatg | 70 | 41 |
| 127158 | 5'UTR | 10 | 169 | caggttggcggacaaagctg | 52 | 42 |
| 127159 | Start Codon | 10 | 192 | cccgacatgtcagacaggtt | 47 | 43 |
| 127160 | Start Codon | 10 | 202 | tggcacgggtcccgacatgt | 62 | 44 |
| 127161 | Start Codon | 10 | 206 | tgcttggcacgggtcccgac | 62 | 45 |
| 127162 | Coding | 10 | 212 | tggccctgcttggcacgggt | 64 | 46 |
| 127163 | Coding | 10 | 222 | gtgtaaactctggccctgct | 73 | 47 |
| 127164 | Coding | 10 | 384 | acaacacatttttcattatt | 60 | 48 |
| 127165 | Coding | 10 | 389 | ttttaacaacaactttttca | 57 | 49 |
| 127166 | Coding | 10 | 394 | gagaattttaacaacaactt | 18 | 50 |
| 127167 | Coding | 10 | 436 | aatctttatttcacgcttaa | 73 | 51 |
| 127168 | Coding | 10 | 447 | aaattctccaaaatctttat | 25 | 52 |
| 127169 | Coding | 10 | 495 | gggtcttttacaatgtctgc | 51 | 53 |
| 127170 | Coding | 10 | 505 | tgctgacacgggtcttttta | 81 | 54 |
| 127171 | Coding | 10 | 554 | attgcttgaagtctgtgttg | 61 | 55 |
| 127172 | Coding | 10 | 559 | gtacaattgcttgaagtctg | 54 | 56 |
| 127173 | Coding | 10 | 564 | gtctggtacaattgcttgaa | 66 | 57 |
| 127174 | Coding | 10 | 569 | ttaacgtgtggtacaattgc | 63 | 58 |
| 127175 | Coding | 10 | 574 | gtctgttaacgtctgctaca | 81 | 59 |
| 127176 | Coding | 10 | 693 | tttctgtgctcatgatcaat | 45 | 60 |
| 127177 | Coding | 10 | 918 | atcctcaccaactgctcata | 52 | 61 |
| 127178 | Coding | 10 | 954 | tagtcatataaatcttctgt | 50 | 62 |
| 127179 | Coding | 10 | 1048 | ttcactgtggacaaagcgtt | 49 | 63 |
| 127180 | Coding | 10 | 1119 | cgtgactggtggtcatatcg | 46 | 64 |
| 127181 | Coding | 10 | 1178 | cctggtccttcacaacagtg | 42 | 65 |
| 127182 | Coding | 10 | 1239 | atgatattggcgctgctgac | 64 | 66 |
| 127183 | Coding | 10 | 1249 | aatccctgacatcatattgg | 52 | 67 |
| 127184 | Coding | 10 | 1259 | gcagtcaagaaatccctgac | 68 | 68 |
| 127185 | Coding | 10 | 1301 | tcactggtgagcctgccaga | 52 | 69 |
| 127187 | 3'UTR | 10 | 1395 | cctctgctcaggcatcagga | 66 | 71 |
| 127188 | 3'UTR | 10 | 1398 | ccacctctgctcacccatca | 72 | 72 |
| 127189 | 3'UTR | 10 | 1432 | ggcgcaagctgcatcaagga | 71 | 73 |
| 127191 | 3'UTR | 10 | 1470 | acacggtgcttctgccgtgt | 59 | 75 |
| 127192 | 3'UTR | 10 | 1480 | aacggttcagacacggtgct | 70 | 76 |
| 127193 | 3'UTR | 10 | 1491 | aatccacaagcaacggttca | 81 | 77 |

As shown in Table 2, SEQ ID NOs 19, 20, 21, 22, 23, 24, 25, 26, 27, 28, 29, 30, 32, 41, 42, 43, 44, 45, 46, 47, 48, 49, 51, 53, 54, 55, 56, 57, 58, 59, 60, 61, 62, 63, 64, 65, 66, 67, 68, 69, 71, 72, 73, 75, 76 and 77 demonstrated at least 40% inhibition of mouse Casein kinase 2-alpha expression in this experiment and are therefore preferred. The target sites to which these preferred sequences are complementary are herein referred to as "active sites" and are therefore preferred sites for targeting by compounds of the present invention.

Example 17

Western Blot Analysis of Casein Kinase 2-alpha Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to Casein kinase 2-alpha is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound up to 50 nucleobases in length comprising at least an 8-nucleobase portion of SEQ ID NO: 20, 21, 22, 23, 24, 25, 26, 27, 28, 30, 32, 34, 35, 37, 38, 39, 40, 41, 42, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 90, 91, 92, 93, 95 or 96 which inhibits the expression of human Casein kinase 2-alpha.

2. The compound of claim 1, which is an antisense oligonucleotide.

3. The compound of claim 2, wherein the antisense oligonucleotide comprises at least one modified internucleoside linkage.

4. The compound of claim 3, wherein the modified internucleLide linkaqe is a phosphorothioate linkage.

5. The compoutd of claim 2, wherein the antisense oligonucleotide comprises at least one modified sugar moiety.

6. The compound of claim 5, wherein the modified sugar moiety is a 2'-O-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A method of inhibiting the expression of Casein kinase 2-alpha in human cells or tissues comprising contacting said cells or tissues in vitro with the compound of claim 1 so that expression of Casein kinase 2-alpha is inhibited.

11. A composition comprising the compound of claim 1 and a pharmaceutically acceptable carrier or diluent.

12. The composition of claim 11 further comprising a colloidal dispersion system.

13. The composition of claim 11 wherein the compound is an antisense oligonucleotide.

14. A compound consisting of SEQ ID NO: 19, 43, 44 or 45.

* * * * *

UNITED STATES PATENT AND TRADEMARK OFFICE
CERTIFICATE OF CORRECTION

PATENT NO.    : 6,607,916 B2
DATED         : August 19, 2003
INVENTOR(S)   : Susan M. Freier Page 1 of 1

It is certified that error appears in the above-identified patent and that said Letters Patent is hereby corrected as shown below:

Title page,
Item [75], Inventors, please delete "Jacqualine" and insert therefor -- Jacqueline --;
Item [56], References Cited, OTHER PUBLICATIONS, "Blanquet," reference, please delete "Neutrophin" and insert therefor -- Neurotrophin --; and
"Pyerin et al.," reference, please delete "600" and insert therefor -- 660 --;

Signed and Sealed this

Twenty-seventh Day of April, 2004

JON W. DUDAS
*Acting Director of the United States Patent and Trademark Office*